US011041146B2

(12) United States Patent
Kurita

(10) Patent No.: US 11,041,146 B2
(45) Date of Patent: Jun. 22, 2021

(54) CELL HAVING ABILITY TO FORM STRATIFIED EPITHELIAL TISSUE, AND METHOD FOR PRODUCING SAME

(71) Applicant: Masakazu Kurita, La Jolla, CA (US)

(72) Inventor: Masakazu Kurita, La Jolla, CA (US)

( * ) Notice: Subject to any disclaimer, the term of this patent is extended or adjusted under 35 U.S.C. 154(b) by 1057 days.

(21) Appl. No.: 15/523,571

(22) PCT Filed: Mar. 30, 2015

(86) PCT No.: PCT/JP2015/059872
§ 371 (c)(1),
(2) Date: Sep. 28, 2017

(87) PCT Pub. No.: WO2016/072105
PCT Pub. Date: May 12, 2016

(65) Prior Publication Data
US 2018/0155695 A1    Jun. 7, 2018

(30) Foreign Application Priority Data
Nov. 4, 2014   (JP) .............................. JP2014-223990

(51) Int. Cl.
| | | |
|---|---|---|
| *C12N 5/10* | (2006.01) | |
| *A61K 35/12* | (2015.01) | |
| *A01K 67/027* | (2006.01) | |
| *C12N 15/09* | (2006.01) | |
| *C12N 15/00* | (2006.01) | |
| *G01N 33/50* | (2006.01) | |
| *C12N 5/077* | (2010.01) | |
| *C12N 5/071* | (2010.01) | |
| *A61K 48/00* | (2006.01) | |
| *C12M 1/00* | (2006.01) | |
| *C12Q 1/02* | (2006.01) | |
| *G01N 33/15* | (2006.01) | |

(52) U.S. Cl.
CPC .............. *C12N 5/10* (2013.01); *A01K 67/027* (2013.01); *A61K 48/00* (2013.01); *C12M 1/00* (2013.01); *C12N 5/0625* (2013.01); *C12N 5/0656* (2013.01); *C12N 15/00* (2013.01); *C12N 15/09* (2013.01); *C12Q 1/02* (2013.01); *G01N 33/15* (2013.01); *G01N 33/50* (2013.01); *G01N 33/5005* (2013.01); *G01N 33/5082* (2013.01); *A61K 35/12* (2013.01); *C12N 2506/1307* (2013.01); *C12N 2510/00* (2013.01); *C12N 2740/16043* (2013.01)

(58) Field of Classification Search
CPC ........................................................ C12N 5/10
USPC ............................................................ 435/325
See application file for complete search history.

(56) References Cited

U.S. PATENT DOCUMENTS

2007/0259383 A1 *  11/2007  Matsui et al.
2007/0269792 A1     11/2007  Bernd et al.

FOREIGN PATENT DOCUMENTS

| JP | 2008-508968 | 3/2008 |
|---|---|---|
| WO | WO 2005/083075 | 9/2005 |
| WO | WO 2012/054896 A1 * | 4/2012 |

OTHER PUBLICATIONS

Boglev, Yeliz, et al. "The unique and cooperative roles of the Grainy head-like transcription factors in epidermal development reflect unexpected target gene specificity." Developmental biology 349.2 (2011): 512-522. (Year: 2011).*
Boglev et al. "The unique and cooperative roles of the Grainy head-like transcription factors in epidermal development reflect unexpected target gene specificity." Developmental biology 349.2 (2011): 512-522. (Year: 2011).*
McDade et al. "Genome-wide analysis of p63 binding sites identifies AP-2 factors as co-regulators of epidermal differentiation." Nucleic acids research 40.15 (2012): 7190-7206. (Year: 2012).*
Wells et al. "Ovol2 suppresses cell cycling and terminal differentiation of keratinocytes by directly repressing c-Myc and Notch1." Journal of Biological Chemistry 284.42 (2009): 29125-29135. (Year: 2009).*
Kaufman et al. "GATA-3: an unexpected regulator of cell lineage determination in skin." Genes & development 17.17 (2003): 2108-2122. (Year: 2003).*
Boldrup et al. "p63 Transcriptionally regulates BNC1, a Pol I and Pol II transcription factor that regulates ribosomal biogenesis and epithelial differentiation." European Journal of Cancer 48.9 (2012): 1401-1406. (Year: 2012).*
Tugores et al. "The epithelium-specific ETS protein EHF/ESE-3 is a context-dependent transcriptional repressor downstream of MAPK signaling cascades." Journal of Biological Chemistry 276.23 (2001): 20397-20406. (Year: 2001).*
Shaoqiong et al. "Related gene expressions in anti-keratinocyte aging induced by Ganoderma lucidum polysaccharides." Journal of medical colleges of PLA 23.3 (2008): 167-175. (Year: 2008).*
Collawn et al. "Adipose-derived stromal cells accelerate wound healing in an organotypic raft culture model." Annals of plastic surgery 68.5 (2012): 501. (Year: 2012).*
Zhang et al. "The multi-differentiation potential of peripheral blood mononuclear cells." Stem cell research & therapy 3.6 (2012): 48. (Year: 2012).*
International Search Report and Written Opinion PCT/JP2015/059872 (WO 2016/072105).
International Search Report and Written Opinion PCT/JP2015/059872 (WO 2016/072105) (English Translation).

(Continued)

*Primary Examiner* — James D Schultz
*Assistant Examiner* — Alexander W Nicol
(74) *Attorney, Agent, or Firm* — William C. Schrot; Jeffrey I. Auerbach; AuerbachSchrot LLC

(57) ABSTRACT

To convert directly from a somatic cell into a cell having the ability to form stratified epithelial tissue that can act as outer skin of the body, a method for producing a cell having the ability to form stratified epithelial tissue is provided, the method including the step of introducing into a somatic cell at least one gene expressed relatively strongly in a cell having the ability to form stratified epithelial tissue.

6 Claims, 13 Drawing Sheets
(7 of 13 Drawing Sheet(s) Filed in Color)

(56) References Cited

OTHER PUBLICATIONS

Tseng et al. (1999) "*Basonuclin in murine corneal and lens epithelia correlates with cellular maturation and proliferative ability*," Differentiation 65:221-227.

Honeycutt et al. (2004) "*Genes Involved in Stem Cell Fate Decisions and Commitment to Differentiation Play a Role in Skin Disease*," J Investigative Dermatology Symposium Proceedings 9(3):261-268.

Kurita et al. "*Trial of direct conversion from fibroblasts to keratinocytes for enhancement of epithelialization of cutaneous ulcers*," Program/proceedings of 22$^{nd}$ Research Council Meeting of Japan Society of Plastic and Reconstructive Surgery; Oct. 10, 2013; O-124.

Kurita et al. "*Trial of direct conversion from fibroblasts to keratinocytes for enhancement of epithelialization of cutaneous ulcers*," Program/proceedings of 22$^{nd}$ Research Council Meeting of Japan Society of Plastic and Reconstructive Surgery; Oct. 10, 2013; O-124 (Translation).

Kurita et al. "*Development towards method of direct conversion from fibroblasts to keratinocytes using gene transduction*," Program/proceedings of 23$^{rd}$ Research Council Meeting of Japan Society of Plastic and Reconstructive Surgery; Sep. 12, 2014; O2-30.

Kurita et al. "*Development towards method of direct conversion from fibroblasts to keratinocytes using gene transduction*," Program/proceedings of 23$^{rd}$ Research Council Meeting of Japan Society of Plastic and Reconstructive Surgery; Sep. 12, 2014; O2-30 (Translation).

McDade et al. (2012) "*Genome-wide analysis of p63 binding sites identifies AP-2 factors as co-regulators of epidermal differentiation*," Nucleic Acids Research 40(15):7190-7206.

Boglev et al. (2011) "*The unique and cooperative roles of the Grainy head-like transcription factors in epidermal development reflect unexpected target gene specificity*," Developmental Biology 349:512-522.

Kurita et al. (2018) "*In vivo reprogramming of wound-resident cells generates skin epithelial tissue*," Nature 561:243 (24 pages).

\* cited by examiner

200 µm

500 µm

— 200 μm

Collagen gel

— 200 μm

CELL HAVING ABILITY TO FORM STRATIFIED EPITHELIAL TISSUE, AND METHOD FOR PRODUCING SAME

CROSS REFERENCE TO RELATED APPLICATIONS AND CLAIM TO PRIORITY

This Application is a national stage application of International Application No. PCT/JP2015/059872, filed Mar. 30, 2015, which claims priority to Japanese Application No. JP2014-223990, filed Nov. 4, 2014, which applications are herein incorporated by reference in their entireties and to which priority is claimed.

TECHNICAL FIELD

The present invention relates to a cell having the ability to form a stratified epithelial tissue induced from a somatic cell, and a method for producing the same. The present invention also relates to a cell preparation for regenerating skins, mucosas or corneal tissues, a method for treating skin, mucosal or corneal ulcer, a method for determining drug efficacy of a test substance for skin, mucosal or corneal disease, and a method for determining exogenous stress on skins, mucosas or corneas, all of which utilize the cell having the ability to form the stratified epithelial tissue. Furthermore, the present invention relates to a composition for preparing a stratified epithelial cell, which induces the stratified epithelial cell from a somatic cell.

BACKGROUND ART

A stratified epithelial tissue protects an inside of a body from external factors such as mechanical disorder and infection at sites contacting the outside world such as epidermis, mucosa and cornea, and at the same time, plays a role of an outer skin for preventing blood and body liquid from leaking and transpiring. The stratified epithelial tissue is formed through stratification by self-replication and differentiation of a precursor cell or a stem cell in a basal layer.

The most representative pathological condition leading to disordered outer skin may include skin ulcers caused by external factors such as burn, trauma, iatrogenic injury (after tumor excision, etc.) and pressure ulcer, and internal factors such as diabetes and peripheral circulatory failure. All factors leading to disordered outer skin may cause ulcers. In addition, the pathological conditions may include digestive tract ulcers leading to disordered outer skin of digestive tract such as oral and anal mucosal defects, corneal ulcers leading to disordered cornea, etc. The skin ulcers causes pain, infection, bleeding, etc., and furthermore it is lethal by itself in a case of a wide region. The mucosal ulcer may cause pain, infection, bleeding and perforated digestive tract. The corneal ulcer causes vision disorder. Due to the advancement in medical science and the prevalence of lifestyle diseases, it is predicted that people suffering from refractory skin ulcers resulting from pressure ulcers, diabetic ulcers and hematogenous disorders as underlying diseases will increase more and more in the future.

Since the epithelial cell has properties as a precursor cell and a stem cell, an ulcerous lesion of epithelium is usually repaired by epithelial cell migration around the ulcer. Thus, in a case of a localized ulcerous lesion, a wound can be healed by keeping the wound clean and protecting it with an ointment or a wound dressing. However, the ulcer becomes refractory when the wounded area is widespread and when there are healing inhibitors such as infection, malnutrition, hyperglycemia and peripheral circulatory disorder. In such a case, treatment is conventionally carried out by implanting a skin from another part of a body through a surgical procedure such as skin grafting and flap plasty. However, many of the patients with ulcers particularly due to pressure ulcer, diabetic ulcer or circulatory disorder have poor general conditions, and thus they have high risks associated with general anesthesia and surgery (see Non-Patent Documents 1 and 2). Moreover, in a case that the wounded area is extremely widespread like a severe burn, the ulcer part cannot be sufficiently reduced and closed only with a remaining self-skin tissue, which may lead to death due to infection or hemodynamic failure. Furthermore, flap plasty is required for a mucosal defect of digestive tract, especially oral cavity, tongue, pharynx or anus composed of stratified epithelium. In addition, for corneal ulcer, corneal implantation may be required in a severe case.

Thus, particularly for severe burns, treatments recently have been conducted by implanting self-epidermal cell sheets prepared by collecting a part of self-skin tissues and culturing the cell. However, patients indicated for this treatment have insufficient absolute amount of the remaining skin tissues and thus insufficient amount of the skin tissues capable of being used for collection and preparation of epidermal cell sheets, and there were many cases that a sufficient amount of epidermal cell sheets could be hardly prepared within a few weeks during which patients could survive without skin implantation.

In addition, in refractory ulcers such as ulcers due to pressure ulcer, diabetic ulcer or circulatory disorder, the wounded area cannot necessarily be closed by surgical procedures such as conventional skin grafting and flap plasty. Since a skin to be implanted should have been collected in the surgical procedures such as skin grafting and flap plasty, there was nothing other than putting a load on the body when the wounded area could not be closed, and thus a means for epithelializing the wound area less invasively and more efficiently has been required.

In recent years, a technique to initialize a somatic cell and induce it into an induced pluripotent stem (iPS) cell by transducing genes encoding Oct3/4, Klf4, c-Myc and Sox2, respectively, into the somatic cell has been reported, and innovative technologies have been provided in the field of regenerative medicine (see Patent Document 1, Non-patent Documents 3 and 4). However, since preparation of an iPS cell and induction from the iPS cell to an epithelial cell take a long time, further technical problems should be solved in order to use this technique for severely burned patients. Also, since the somatic cell is again induced to the epithelial cell from a state that the somatic cell has acquired pluripotency in the iPS cell preparation process, there are various problems to be solved in the pluripotent state such as the possibility of canceration, and moreover, the production efficiency is poor, thus further technical problems should be solved in order to use the iPS cell for patients with refractory skin ulcer, mucosal ulcer, corneal ulcer, etc. with relatively slow disease progression.

On the other hand, in the course of development, a somatic cell for which the cell lineage has once fixed continues to proliferate and differentiate within the same cell lineage. In contrast, a transformation of a cell lineage which cannot be physiologically observed is called direct conversion, and techniques of the direct conversion from a skin fibroblast to a muscle cell (Non-Patent Document 3), a neural cell (see Non-Patent Document 6), a cardiomyocyte (see Non-Patent Document 7), a hepatocyte (see Non-Patent Document 8), a blood stem cell (see Non-Patent Document 9), etc. have been reported.

With such a prior art as a background, it is desired to develop a cell which can be directly induced from a somatic cell represented by skin fibroblasts and adipose-derived mesenchymal cells and has the ability of forming a stratified epithelial tissue capable of serving as an outer skin of a body, and to achieve provision of a cell source capable of being broadly used for treating skin ulcers. However, there has been no report that a somatic cell is directly converted to a cell having the ability to form a stratified epithelial tissue.

PRIOR ART DOCUMENTS

Patent Documents

Patent Document 1: WO2007/069666

Non-Patent Documents

Non-Patent Document 1: Kurita M, Ichioka S, Oshima Y, Harii K, "Scand J Plast Reconstr Surg Hand Surg", 2006, 40(4), p 214-218
Non-Patent Document 2: Kurita M, Ichioka S, Tanaka Y, Umekawa K, Oshima Y, Ohura N, Kinoshita M, Harii K, "Wound Repair Regenes", 2009, 17, p 312-317
Non-Patent Document 3: Takahashi K, Yamanaka S, "Cell", 2006, 25, 126(4), p 663-676
Non-Patent Document 4: Takahashi K, Tanabe K, Ohnuki M, Narita M, Ichisaka T, Tomoda K, Yamanaka S, "Cell", 2007 Nov. 30, 131(5), p 861-72
Non-Patent Document 5: Davis R L, Weintraub H, Lassar A B, "Cell", 1987 Dec. 24, 51(6), p 987-1000
Non-Patent Document 6: Vierbuchen T1, Ostermeier A, Pang Z P, Kokubu Y, Sudhof T C, Wernig M, "Nature", 2010 Feb. 25, 463(7284), p 1035-1041
Non-Patent Document 7: Ieda M, Fu J D, Delgado-Olguin P, Vedantham V, Hayashi Y, Bruneau B G, Srivastava D, "Cell", 2010 Aug. 6, 142(3), p 375-386
Non-Patent Document 8: Sekiya S1, Suzuki A, "Nature", 2011 Jun. 29, 475(7356), p 390-393

SUMMARY OF INVENTION

Problem to be Solved

Thus, in order to solve the aforementioned problems of the prior art, one of objects of the present invention is to directly convert a somatic cell to a cell having the ability to form a stratified epithelial tissue capable of serving as an outer skin of a body. More specifically, an object of the present invention is to establish a technique for providing a source of a cell having the ability to form a stratified epithelial tissue serving as an outer skin (skin, mucosa, corneal epithelium) which covers a free surface on the inside and outside of a body. Also, an object of the present invention is to provide various applications of the cell having the ability to form the stratified epithelial tissue induced from such a somatic cell.

Solution to Problem

In order to solve the aforementioned problems, the inventors selected a skin fibroblast as a representative somatic cell and a keratinocyte collected from a skin as a representative cell having the ability to form a stratified epithelial tissue capable of serving as an outer skin, and examined genes expressed in each cell using data of a DNA microarray and a microRNA microarray, so as to find that a cell having a morphology and properties equivalent to those of the keratinocyte could be produced by transduction of a gene which was expressed specific to or relatively strongly to the keratinocyte. It was actually confirmed that the induced fibroblast obtained in such a way could proliferate by a monolayer culture or a feeder culture optimized for keratinocyte proliferation and expressed a marker specific to the keratinocyte. Furthermore, it was confirmed that the induced fibroblast exhibited a self-replication ability and terminal differentiation under the monolayer culture conditions. Furthermore, it was confirmed that the stratified epithelial tissue could be formed when the induced fibroblast was subjected to a three-dimensional culture using a collagen gel containing a skin fibroblast as a scaffold. Based on these findings, the present invention was completed by further investigations.

That is, the present invention provides the inventions of the following aspects.

Item 1. A production method of a cell having ability to form a stratified epithelial tissue, comprising a step of transducing at least one gene which is relatively strongly expressed in the cell having the ability to form the stratified epithelial tissue, into a somatic cell.

Item 2. A production method of a cell having ability to form a stratified epithelial tissue, comprising a step of transfecting one or more genes selected from GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene, into a somatic cell.

Item 3. A production method of a cell having ability to form a stratified epithelial tissue, comprising a step of transfecting (1) TFAP2A gene or TFAP2C gene, (2) GRHL family genes, (3) BNC1 gene, and (4) MYC family genes, into a somatic cell.

Item 4. A production method of a cell having the ability to form a stratified epithelial tissue, comprising a step of transfecting (1) TFAP2A gene or TFAP2C gene, (2) GRHL family genes, (3) BNC1 gene, (4) MYC family genes, and (5) at least one gene which are relatively strongly expressed in the cell having the ability to form the stratified epithelial tissue, into a somatic cell.

Item 5. A production method of a cell having ability to form a stratified epithelial tissue, comprising a step of transfecting (1) TFAP2A gene, (2) GRHL2 gene, (3) BNC1 gene, and (4) c-MYC gene, into a somatic cell.

Item 6. A production method of a cell having ability to form a stratified epithelial tissue, comprising a step of transfecting GATA3 gene, TFAP2A gene, GRHL2 gene, TP63 gene, BNC1 gene, EHF gene, ZNF165 gene and c-MYC gene, into a somatic cell.

Item 7. A production method of a cell having ability to form a stratified epithelial tissue, comprising a step of transfecting OVOL1 gene, TFAP2A gene, GRHL2 gene, BNC1 gene, LASS3 gene, ZBED2 gene, SOX7 gene, SOX9 gene and c-MYC gene, into a somatic cell.

Item 8. A production method of a cell having ability to form a stratified epithelial tissue, comprising a step of transfecting GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene, into a somatic cell.

Item 9. The production method of the cell having the ability to form the stratified epithelial tissue according to any one of Items 1 to 8, wherein the somatic cell is derived from human.

Item 10. The production method of the cell having the ability to form the stratified epithelial tissue according to any one of Items 1 to 9, wherein the somatic cell is a skin fibroblast.

Item 11. The production method of the cell having the ability to form the stratified epithelial tissue according to any one of Items 1 to 9, wherein the somatic cell is an adipose-tissue derived stromal cell.

Item 12. The production method of the cell having the ability to form the stratified epithelial tissue according to any one of Items 1 to 9, wherein the somatic cell is a mononuclear cell in a peripheral circulating blood.

Item 13. A cell having ability to form a stratified epithelial tissue produced by the production method according to any one of Items 1 to 12.

Item 14. A cell preparation comprising the cell having the ability to form the stratified epithelial tissue according to Item 13.

Item 15. The cell preparation according to Item 14, comprising a scaffold material.

Item 16. The cell preparation according to Item 15, wherein the scaffold material is a collagen.

Item 17. The cell preparation according to any one of Items 14 to 16, which is used for regenerating a stratified epithelium, a skin tissue, a mucosal tissue or a corneal tissue.

Item 18. The cell preparation according to any one of Items 14 to 17, which is a sheet-shaped epithelial cell sheet.

Item 19. A non-human mammal with a stratified epithelial tissue formed, which is produced by administering the cell having the ability to form a stratified epithelial tissue according to Item 12 to the non-human mammal so as to form the stratified epithelial tissue from the cell having the ability to form the stratified epithelial tissue in the body of the mammal.

Item 20. A method for determining drug efficacy of a test substance on an epithelial tissue, comprising a step of determining the drug efficacy of the test substance on the epithelial tissue by administering the test substance to the non-human mammal according to Item 19.

Item 21. A method for determining influence of an external factor on the epithelial tissue, comprising a step of determining a stress on the epithelial tissue by loading stress such as an anticancer agent and radiation on the non-human mammal according to Item 19.

Item 22. A composition for adjusting a cell having the ability to form a stratified epithelial tissue, comprising the gene transfected into the somatic cell according to any one of Items 1 to 8.

Item 23. The composition for adjusting the cell according to Item 21, wherein the gene is comprised in a form capable of being transduced into the somatic cell.

Item 24. An epithelium-like tissue prepared by culturing the cell having the ability to form the stratified epithelial tissue according to Item 13.

Item 25. A method for analyzing drug efficacy of a test substance on an epithelial tissue, comprising a step of analyzing the drug efficacy of the test substance on an epithelial-like tissue by administering the test substance to the epithelial-like tissue prepared through culturing a cell having the ability to form a stratified epithelial tissue produced by transfecting the gene according to any one of Items 1 to 8 into a somatic cell taken from an animal.

Item 26. A method for analyzing influence of an external factor on an epithelial tissue, comprising a step of analyzing a stress on an epithelial-like tissue by loading a stress such as an anticancer agent and radiation on the epithelial-like tissue prepared by culturing a cell having the ability to form a stratified epithelial tissue produced by transfecting the gene according to any one of Items 1 to 8 into a somatic cell taken from an animal.

Item 27. A kit of a vector specialized for transfecting the gene according to any one of Items 1 to 8 into the somatic cell.

Effects of Invention

According to the present invention, a cell having the ability to form a stratified epithelial tissue can be provided, which has properties equivalent to those of keratinocytes, digestive tract epithelial cells and corneal epithelial cells. In addition, this cell having the ability to form the stratified epithelial tissue can provide a medical means or a cell preparation effective for treating a pathological condition associated with outer skin tissue ulcers including skin ulcers, digestive tract ulcers and corneal ulcer, such as burn, trauma, pressure ulcer, diabetes and peripheral circulatory disorder. In addition, according to the present invention, for not only the skin ulcers but also a wide range of diseases occurring on epithelium such as epidermis, digestive tract epithelium and corneal epithelium, the cell having the ability to form the stratified epithelial tissue is prepared from a somatic cell of a patient (not limited to somatic cells of a patient. For example it may include blood, adipose-tissue stromal cell, etc.), and the prepared cell is subjected to various analyses, contributing to clarification of pathological condition or treatment of a disease. Particularly, the cell having the ability to form the stratified epithelial tissue prepared from a human somatic cell is suitable also from the aspect of confirmation of the drug efficacy as a material for drug discovery and drug development. In addition, the cell can contribute to clarification of a pathological condition originating from an epithelial stem cell such as cancer, by using the cell having the ability to form the stratified epithelial tissue having opposing properties, self-replication ability and terminal differentiation.

BRIEF DESCRIPTION OF DRAWINGS

The patent or application file contains at least one drawing/photograph executed in color. Copies of this patent or patent application publication with color drawing(s) will be provided by the Office upon request and payment of the necessary fee.

DESCRIPTION OF EMBODIMENTS

Figure 1:
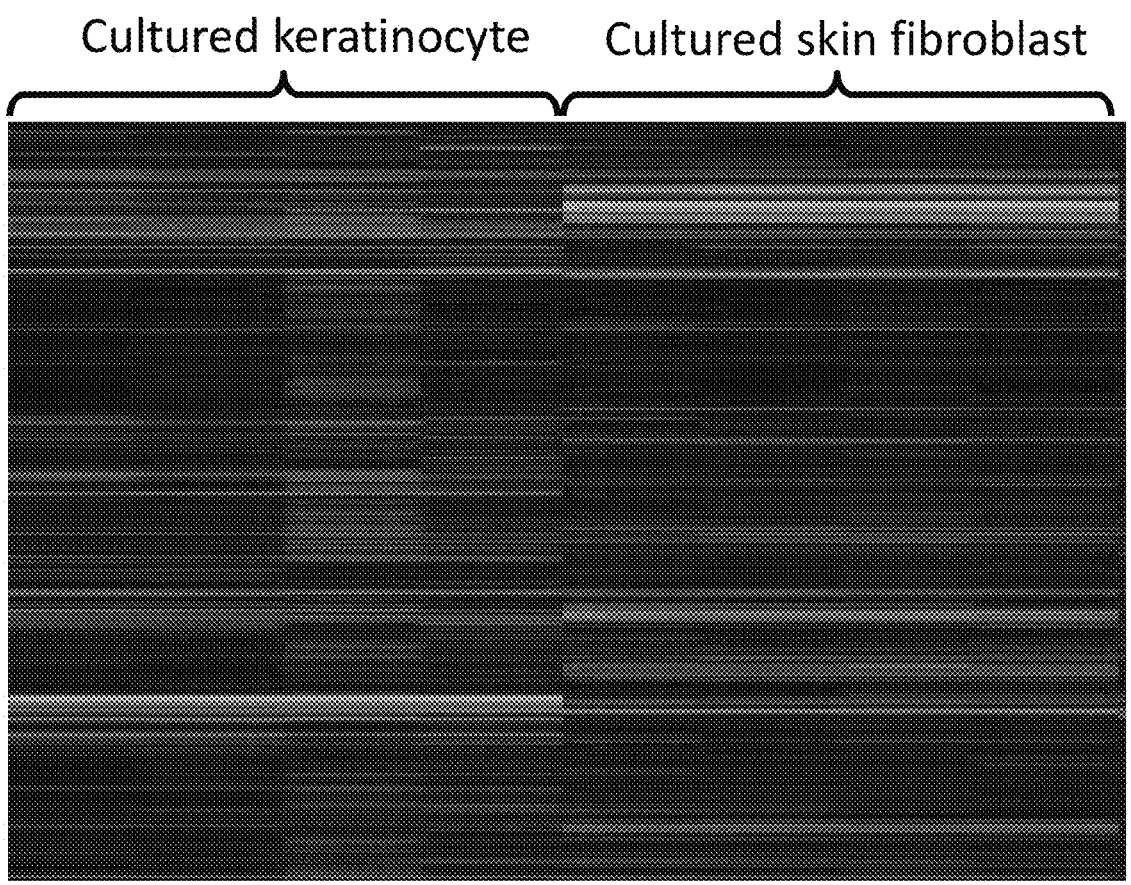
FIG. 1 illustrates a view showing data obtained by evaluating mRNA expressions of a cultured keratinocyte and a cultured fibroblast using a microarray, in a form of heat map. This data is based on data obtained from a database (Accession: GDS1505 ID: 1505) provided by NCBI in U.S.

1. Production Method and Application for a Cell Having the Ability to Form a Stratified Epithelial Tissue In the present invention, the term "cell having the ability to form the stratified epithelial tissue" means a cell having an ability of serving as a stratified epithelium precursor cell or a stem cell which protects the inside of the body from external factors such as mechanical disorder and infection at sites contacting the outside world such as epidermis, mucosa and cornea (in other word, epithelial stem cell), and also includes keratinocytes, digestive tract epithelial cells, corneal epithelial cells which are somatic cells in a living body, as well as cells which are artificially derived from somatic cells by the present invention. The cell having the ability to form the stratified epithelial tissue exhibits both the properties of the self-replication ability and the terminal differentiation by adjusting the culture conditions under the monolayer culture conditions. Alternatively, the cell having the ability to form the stratified epithelial tissue has an ability of forming a stratified epithelial tissue-like structure in the three-dimensional culture comprising the collagen gel containing skin fibroblasts or the like as a carrier.

The production method of the cell having the ability to form the stratified epithelial tissue of the present invention characteristically comprises a step of transducing at least one gene which is relatively strongly expressed in the cell having the ability to form the stratified epithelial tissue (e.g. keratinocyte, digestive tract epithelial cell or corneal epithelial cell) into a somatic cell. Hereinafter, the gene to be transduced into the somatic cell will be referred to as "transgene". As the transgene, a plurality of genes which are relatively strongly expressed in the cell having the ability to form the stratified epithelial tissue may be transduced, and in addition to the gene relatively strongly expressed in the cell having the ability to form the stratified epithelial tissue, genes which are not relatively strongly expressed may be combined.

Herein, the "transgene" also includes not only a gene encoding a protein but also a noncoding RNA such as a microRNA. In addition, the "gene relatively strongly expressed in the cell having the ability to form the stratified epithelial tissue" means a gene of which the expression level in the cell having the ability to form the stratified epithelial tissue has been confirmed to be higher than that in a mesenchymal cell such as a skin fibroblast by a quantitative evaluation method for gene expression levels such as real-time PCR method and microarray. Note that the "gene not relatively strongly expressed" means a gene of which the expression level in the cell having the ability to form the stratified epithelial tissue is lower than that in the mesenchymal cell.

The gene relatively strongly expressed in the cell having the ability to form the stratified epithelial tissue includes at least the following genes encoding a protein: TFAP2A gene, TFAP2C gene, GRHL family genes (GRHL1 gene, GRHL2 gene, and GRHL3 gene, etc.), GATA3 gene, OVOL1 gene, OVOL2 gene, ESRP1 gene, ESRP2 gene, TP63 gene, DNP63A gene, MAPK13 gene, ARNTL2 gene, LASS3 gene, EHF gene, ZNF165 gene, ZNF750 gene, ZBED2 gene, IRX4 gene, SOX7 gene, SOX9 gene, FOXQ1 gene, PPP1R13L gene, and KLF4 gene. The gene relatively strongly expressed in the cell having the ability to form the stratified epithelial tissue also includes at least the following noncoding RNAs: mir-182, mir-183, mir-96, mir-200b, mir-200a, mir-429, mir-200c, mir-141, mir-203, mir-205, mir-135b, mir-17, mir-18a, mir-19a, mir-19b-1, mir-20a, mir-92a-1, and mir-367.

In particular, the production method of the cell having the ability to form the stratified epithelial tissue of the present invention preferably comprises a step of transducing at least one gene selected from (1) TFAP2A gene or TFAP2C gene and (2) GRHL family genes, and at least one gene selected from (3) BNC1 gene and (4) MYC family genes, into a somatic cell. Furthermore, in addition to (1) to (4), (5) at least one gene which is relatively strongly expressed in a cell having the ability to form the stratified epithelial tissue may be transduced.

The GRHL family genes may include GRHL1 gene, GRHL2 gene, GRHL3 gene, etc. Each of these GRHL family genes may be used alone or in a combination of two or more genes. The Myc family genes may include c-Myc, N-Myc, L-Myc, etc. Each of these Myc family genes may be used alone or in a combination of two or more genes. Among these Myc family genes, preferably the c-Myc gene or the L-Myc gene, more preferably the c-Myc gene is used in the present invention. The c-Myc gene is known as a transcriptional regulator involved in cell differentiation and proliferation (S. Adhikary, M. Elilers, Nat. Ray. Mol. Cell Biol., 6, pp 635-645, 2005), and their base sequences are known (see Table 1).

Also, in other methods of producing the cell having the ability to form the stratified epithelial tissue of the present invention, all or some of genes: GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene are transduced into the somatic cell in order to induce the cell having the ability to form the stratified epithelial tissue from the somatic cell.

In the present invention, among the genes transduced into the somatic cell, the TFAP2A gene, GRHL2 gene, BNC1 gene and c-MYC gene are particularly important, but functional characteristics according to the purposes, such as enhancements of cellular proliferative potency, stratificational differentiative potency and cellular migratory potency can be provided by gene transduction in combination with other genes. For example, when comparing the production method comprising the step of transfecting GATA3 gene, TFAP2A gene, GRHL2 gene, TP63 gene, BNC1 gene, EHF gene, ZNF165 gene and c-MYC gene into the somatic cell with the production method comprising the step of transfecting OVOL1 gene, TFAP2A gene, GRHL2 gene, BNC1 gene, LASS3 gene, ZBED2 gene, SOX7 gene, SOX9 gene and c-MYC gene into the somatic cell, the former can increase the terminal differentiative potency, and the latter can increase the proliferative potency.

The base sequences of any genes used in the present invention are known (Table 1). Note that, NCBI in this specification is an abbreviation for National Center for Biotechnology Information in U.S., and Accession numbers in Table 1 are also registered in a database provided by NCBI.

TABLE 1

| Gene | Human Reference sequences | transcript variant | Mouse Reference sequences | transcript variant |
| --- | --- | --- | --- | --- |
| GATA3 | NM_001002295.1 | transcript variant 1 | NM_008091.3 | |
|  | NM_002051.2 | transcript variant 2 | | |
| OVOL1 | NM_004561.3 | | NM_019935.3 | |
| OVOL2 | NM_021220.2 | | NM_026924.3 | transcript variant A |
|  | | | NM_152947.2 | transcript variant B |
| ESRP1 | NM_017697.3 | transcript variant 1 | NM_194055.3 | transcript variant 1 |
|  | NM_001034915.2 | transcript variant 2 | NM_001290383.1 | transcript variant 2 |
|  | NM_001122826.1 | transcript variant 3 | | |
|  | NM_001122825.1 | transcript variant 4 | | |
|  | NM_001122827.1 | transcript variant 5 | | |
| ESRP2 | NM_024939.2 | | NM_176838.2 | |
| GRHL1 | NM_198182.2 | | NM_001161406.1 | transcript variant 1 |
|  | | | NM_145890.2 | transcript variant 2 |
| GRHL2 | NM_024915.3 | | NM_026496.4 | |
| GRHL3 | NM_021180.3 | transcript variant 1 | NM_001013756.1 | |
|  | NM_198173.2 | transcript variant 2 | | |
|  | NM_198174.2 | transcript variant 3 | | |
|  | NM_001195010.1 | transcript variant 4 | | |
| TFAP2A | NM_003220.2 | transcript variant 1 | NM_011547.4 | transcript variant 1a |
|  | NM_001032280.2 | transcript variant 2 | NM_001301674.1 | transcript variant 1b |
|  | NM_001042425.1 | transcript variant 3 | NM_001122948.2 | transcript variant 3 |

TABLE 1-continued

| Gene | Human Reference sequences | transcript variant | Mouse Reference sequences | transcript variant |
|---|---|---|---|---|
| TFAP2C | NM_003222.3 | | NM_009335.2 | transcript variant 1 |
| | | | NM_001159696.1 | transcript variant 2 |
| TP63 | NM_003722.4 | transcript variant 1 | NM_001127259.1 | transcript variant 1 |
| | NM_001114978.1 | transcript variant 2 | NM_001127260.1 | transcript variant 2 |
| | NM_001114978.1 | transcript variant 3 | NM_001127261.1 | transcript variant 3 |
| | NM_001114980.1 | transcript variant 4 (DNP63A) | NM_011641.2 | transcript variant 4 (DNp63A) |
| | NM_001114981.1 | transcript variant 5 | NM_001127264.1 | transcript variant 5 |
| | NM_001114982.1 | transcript variant 6 | NM_001127262.1 | transcript variant 6 |
| | | | NM_001127263.1 | transcript variant 7 |
| | | | NM_001127265.1 | transcript variant 8 |
| MAPK13 | NM_002754.4 | | NM_011950.2 | |
| ARNTL2 | NM_020183.4 | transcript variant 1 | NM_172309.2 | transcript variant 1 |
| | NM_001248002.1 | transcript variant 2 | NM_001289679.1 | transcript variant 2 |
| | NM_001248003.1 | transcript variant 3 | NM_001289680.1 | transcript variant 3 |
| | NM_001248004.1 | transcript variant 4 | NM_001289681.1 | transcript variant 4 |
| | NM_001248005.1 | transcript variant 5 | | |
| BNC1 | NM_001717.3 | transcript variant 1 | NM_007562.2 | |
| | NM_001301206.1 | transcript variant 2 | | |
| LASS3 | NM_001290341.1 | transcript variant 1 | NM_001164201.1 | |
| | NM_001290342.1 | transcript variant 2 | | |
| | NM_001290343.1 | transcript variant 3 | | |
| | NM_178842.3 | transcript variant 4 | | |
| EHF | NM_001206616.1 | transcript variant 1 | NM_007914.3 | |
| | NM_012153.5 | transcript variant 2 | | |
| | NM_001206615.1 | transcript variant 3 | | |
| ZNF165 | NM_003447.3 | | | |
| ZNF750 | NM_024702.2 | | NM_178763.4 | |
| ZBED2 | NM_024508.4 | | | |
| ID1 | NM_002165.3 | transcript variant 1 | NM_010495.3 | |
| | NM_181353.2 | transcript variant 2 | | |
| IRX2 | NM_033267.4 | transcript variant 1 | NM_010574.2 | |
| | NM_001134222.1 | transcript variant 2 | | |
| IRX4 | NM_001278633.1 | transcript variant 2 | | |
| | NM_001278634.1 | transcript variant 3 | | |
| | NM_001278635.1 | transcript variant 4 | | |
| | NM_016358.2 | transcript variant 5 | | |
| SOX7 | NM_031439.3 | | NM_011446.1 | |
| SOX9 | NM_000346.3 | | NM_011448.4 | |
| KLF4 | NM_004235.4 | | NM_010637.3 | |
| c-MYC | NM_002467.4 | | NM_001177352.1 | transcript variant 1 |
| | | | NM_001177354.1 | transcript variant 1 |
| | | | NM_001177353.1 | transcript variant 2 |
| | | | NM_001177354.1 | transcript variant 2 |
| N-MYC | NM_001293228.1 | transcript variant 1 | NM_008709.3 | |
| | NM_001293233.1 | transcript variant 2 | | |
| | NM_005378.5 | transcript variant 2 | | |
| | NM_001293231.1 | transcript variant 3 | | |
| L-MYC | NM_001033081.2 | transcript variant 1 | NM_008506.2 | |
| | NM_001033082.2 | transcript variant 2 | | |
| | NM_005376.4 | transcript variant 3 | | |
| FOXQ1 | NM_033260.3 | | NM_008239.4 | |
| PPP1R13L | NM_001142502.1 | transcript variant 1 | NM_001010836.3 | |
| | NM_006663.3 | transcript variant 2 | | |
| mir-182 | MI0000272 | | MI0000224 | |
| mir-183 | MI0000273 | | MI0000225 | |
| mir-96 | MI0000098 | | MI0000583 | |
| mir-200b | MI0000342 | | MI0000243 | |
| mir-200a | MI0000737 | | MI0000554 | |
| mir-429 | MI0001641 | | MI0001642 | |
| mir-200c | MI0000650 | | MI0000694 | |
| mir-141 | MI0000457 | | MI0000166 | |
| mir-203 | MI0000283 | | MI0000246 | |
| mir-205 | MI0000285 | | MI0000248 | |
| mir-135b | MI0000810 | | MI0000646 | |
| mir-17 | MI0000071 | | MI0000687 | |
| mir-18a | MI0000072 | | MI0000567 | |
| mir-19a | MI0000073 | | MI0000688 | |
| mir-19b-1 | MI0000074 | | MI0000718 | |
| mir-20a | MI0000076 | | MI0000568 | |
| mir-92a-1 | MI0000093 | | MI0000719 | |
| mir-367 | MI0000775 | | MI0000775 | |

Many of these genes are commonly originated in mammals including humans, and although a gene derived from any mammal can be used, it is preferable to appropriately select a gene according to an origin of a somatic cell to be transduced. For example, in the case of using a human-derived somatic cell, the transgene is preferably derived from a human. Also, the transgene may be, in addition to the wild-type gene, a mutated gene encoding a mutated gene product which has several (e.g. 1 to 10, preferably 1 to 6, more preferably 1 to 4, even more preferably 1 to 3, particularly preferably 1 or 2) amino acids substituted, deleted, and/or inserted in an amino acid sequence of the gene product, and has functions equivalent to those of a wild-type gene product.

In the present invention, the aforementioned transgene can be prepared according to a conventional method on the basis of a known sequence information. For example, a cDNA of a targeted gene can be prepared by extracting an RNA from a cell derived from a mammal and cloning it according to the conventional method.

In the present invention, as the "somatic cell" from which the cell having the ability to form the stratified epithelial tissue is induced, its kind is not particularly limited, and cells derived from any tissues or sites can be used. The somatic cell used in the present invention is exemplified by cells derived from tissues such as skin, subcutaneous fat, muscle, placenta, bone, cartilage, blood and corneal stroma, more specifically, skin fibroblast, subcutaneous adipose-tissue derived stromal cell (subcutaneous fat cell), embryonic fibroblast, adipocyte, muscle cell, osteoblast, chondrocyte, mononuclear cell in circulating blood, keratocyte in corneal stroma, etc. Among them, the skin-derived cell, subcutaneous fat-derived cell or blood-derived cell are preferable, and the skin fibroblast, subcutaneous adipose-tissue derived stromal cell and mononuclear cell in circulating blood are particularly preferable, from the viewpoint of preparing a cell having minimal invasiveness to a living body and capable of more efficiently forming the stratified epithelial tissue. Like this, it is clinically advantageous that a material can be selected from various cells, and particularly easily-available cells such as skin-derived cell, subcutaneous fat-derived cell, mononuclear cell in circulating blood can also be used, also from the viewpoints of reduction of the burden on the patient and stable availability of the cells. Additionally, as the somatic cell, a commercially available product may be used, and a somatic cell differentiated from an ES cell, a mesenchymal stem cell, etc. may be used.

In addition, although the somatic cell is appropriately selected from cells derived from mammals such as human, mouse, rat, hamster, rabbit, cat, dog, sheep, pig, cattle, goat, monkey depending on the intended use of the cell having the ability to form the stratified epithelial tissue, the human-derived cell is preferable in a case of use for a human such as treatment of human, clarification of pathology and confirmation of the drug efficacy. In addition, when a human-derived somatic cell is used, the cell may be derived from any of a fetus, an infant, a child and an adult. When the cell having the ability to form the stratified epithelial tissue is used for the purposes of treatment of human, clarification of pathology, confirmation of the drug efficacy, etc., a somatic cell collected from a patient is preferably used.

Transduction of the transgene into a somatic cell can be carried out by a method conventionally used in transfection of an animal cell. Specifically, the method for transducing the transgene into the somatic cell is exemplified by a method using a vector; a calcium phosphate method; a lipofection method; an electroporation method; a microinjection method, etc. Among them, the method using a vector is preferable from the viewpoint of transduction efficiency. When transducing the transgene into a somatic cell using a vector, a virus vector, a non-viral vector, an artificial virus, etc. can be used as a vector, but a viral vector such as an adenovirus, retrovirus and lentivirus is suitably used from the viewpoint of safety. Note that, in a case that the vectors are used and a plurality of the aforementioned transgenes are used, each gene may be incorporated into different vectors, or alternatively two or more transgenes may be incorporated in one vector.

In such a way, the cell having the ability to form the stratified epithelial tissue can be induced from the somatic cell into which the transgene has been transduced. The cell from which the cell having the ability to form the stratified epithelial tissue is induced can be selected according to, as indicators, the presence or absence of proliferative potency under a culture condition suitable for the separation and amplification of keratinocyte, and of properties as the epithelial cell. Since such a cell having the ability to form the stratified epithelial tissue specifically exhibits a higher proliferative potency compared to a cell which has acquired an ability of forming the stratified epithelial tissue by culture on a feeder cell (obtained by inactivating the proliferative potency in a 3T3-J2 feeder cell, a 3T3 cell, a mouse embryonic fibroblast, a human skin fibroblast, etc. by mitomycin C or radiation) suitable for isolation and proliferation of keratinocytes, or on a keratinocyte serum-free medium, the cell having the ability to form the stratified epithelial tissue can be selected by continuing passage processes. Also it is effective to add an Rho kinase inhibitor (Y27632, etc.) capable of relatively improving the frequency of the keratinocyte division on the feeder. In addition, a purity of the cell having the ability to form the stratified epithelial tissue can be increased by flow cytometry and cell separation using a magnetic cell separation device, using a surface antigen (Epi-CAM etc.) specific to epithelial cells. In addition, when a reporter gene construct prepared by previously linking a drug resistance gene to a promoter of an epithelial cell marker gene (CDH1, Epi-CAM, etc.) has been transduced into a somatic cell, a cell which has acquired the properties of the epithelial cell can grow in the presence of drugs, and thus the cell can also be selected depending on the growth in the presence of the drugs as an indicator.

The cell having the ability to form the stratified epithelial tissue obtained in such a way can be proliferated by culture in a liquid medium containing an Rho kinase inhibitor on a feeder, and can be safely proliferated while maintaining the stratified epithelial tissue-forming ability until about 10 to 20 passages for conventional passage. For culturing the cell having the ability to form the stratified epithelial tissue, a medium conventionally used for culturing an animal cell can be used. One suitable medium used for culturing the cell having the ability to form the stratified epithelial tissue is exemplified by a serum-free keratinocyte medium (Keratinocyte-SFM, Life technologies, Inc.) etc. Addition of a cytokine for accelerating proliferation of a keratinocytes under a culture condition, such as bFGF, and various pharmacologically active substances is also useful.

The cell having the ability to form the stratified epithelial tissue obtained in such a way can form a stratified epithelial tissue in vivo on an extracellular matrix including a mesenchymal cell such as a skin fibroblast and an adipose-tissue derived stromal cell, e.g. on a wounded area of skin ulcer. Furthermore, an epithelium-like tissue having a stratified squamous epithelium-like three-dimensional structure can be formed by culturing it on a collagen gel containing a mesenchymal cell such as a skin fibroblast and an adipose-tissue derived stromal cell in vitro to form an air-liquid interface.

Like this, the cell having the ability to form the stratified epithelial tissue obtained in the present invention has a proliferative potency and can regenerate the stratified epithelial tissue inside and outside a living body, and thus, it is effective for treating skin ulcers resulting from burn, trauma, iatrogenic injury (after tumor excision, etc.), pressure ulcer, diabetes and peripheral circulatory disorder, ulcers of digestive tract such as nasal cavity, oral cavity and perianal mucosa, and corneal ulcers, and can be used as a cell preparation (pharmaceutical composition) for regenerating an epithelial tissue. The cell having the ability to form the stratified epithelial tissue may be applied alone as it is for a diseased site of skin, digestive tract or cornea.

When the cell having the ability to form the stratified epithelial tissue is prepared as a cell preparation for regenerating epithelial tissue, the preparation may contain the cell having the ability to form the stratified epithelial tissue, and if necessary, a pharmaceutically acceptable carrier for dilution. Herein, the pharmaceutically acceptable carrier for dilution is exemplified by saline, buffer, etc. Furthermore, if necessary, the cell preparation may contain a pharmacologically active component or a component serving as a nutrient source for the cell having the ability to form the stratified epithelial tissue.

The cell having the ability to form the stratified epithelial tissue may be applied to diseased sites of a skin, a digestive tract and a cornea, as an epithelial cell sheet forming the stratified epithelium-like tissue under a culture condition.

When the cell having the ability to form the stratified epithelial tissue is prepared as an epithelial cell sheet for regenerating the epithelial tissue, the cell having the ability to form the stratified epithelial tissue may be combined with a pharmacologically active component or a component serving as a nutrient source for the cell having the ability to form the stratified epithelial tissue, if necessary.

After an epithelium-like tissue having a stratified squamous epithelium-like three-dimensional structure is prepared using, as a scaffold, an extracellular matrix like a collagen containing a mesenchymal cell such as a skin fibroblast and an adipose-tissue derived stromal cell, the cell having the ability to form the stratified epithelial tissue may be applied to diseased sites of a skin, a digestive tract and a cornea.

When the cell having the ability to form the stratified epithelial tissue is prepared as an epithelium-like tissue having a three-dimensional structure for regenerating the epithelial tissue, the cell having the ability to form the stratified epithelial tissue may be combined with the pharmacologically active component or the component serving as a nutrient source for the cell having the ability to form the stratified epithelial tissue, if necessary. The use of the scaffold material in such a way can allow the stratified epithelium-like structure to more promptly form at the implantation site, and further enhance the regeneration of the epithelial tissue.

The usable scaffold material is not particularly limited as long as it is pharmaceutically acceptable, and is appropriately selected depending on the site of the cartilage tissue to be applied, and for example, it is exemplified by a gel-like biocompatible material. The usable scaffold material is preferably exemplified by a collagen, a fibronectin, a hyaluronic acid, a complex thereof, etc. As for these scaffold materials, one kind may be used alone, and a combination of two or more kinds may also be used.

Also, the shape of the scaffold material is not particularly limited, and it may be appropriately designed according to the shape of the injured site on the epithelial tissue to which the cell preparation is applied.

The method for applying the cell preparation to a diseased site of the epithelial tissue is appropriately set according to the type of the cell preparation, the site of the epithelial tissue to be applied, etc., and it is exemplified by a method for directly spraying the cell preparation to the site of the skin ulcer to be treated, a method for suturing and fixing a sheet and a three-dimensional structure according to a skin grafting technique, and the like.

In relation to the dose of the cell preparation applied to the diseased site of epithelial tissue, an amount effective for regenerating the epithelial tissue should be appropriately set on the basis of the type of the cell preparation, the site of the epithelial tissue, the degree of the symptom, the age and sex of the patient, etc.

In addition, a non-human mammal dosed with the cell having the ability to form the stratified epithelial tissue and having an epithelial tissue formed from the cell having the ability to form the stratified epithelial tissue can be used as a tool for determining and analyzing the drug efficacy of the test substance on the epithelial tissue. That is, the test substance is administered to the non-human mammal having the epithelial tissue formed from the cell having the ability to form the stratified epithelial tissue, and the drug efficacy of the test substance on the epithelial tissue is determined and analyzed, and thereby the drug efficacy of the test substance on the epithelial tissue can be determined and analyzed. Herein, the test substance means a substance to be subjected to determination and analysis for the drug efficacy on the epithelial tissue, and specifically it is exemplified by a candidate substance for a therapeutic drug for epithelial diseases. As the non-human mammal, mouse, rat, hamster, rabbit, cat, dog, sheep, pig, cattle, goat, monkey or the like is appropriately selected.

In addition, the non-human mammal having the epithelial tissue formed from the cell having the ability to form the stratified epithelial tissue can be used as a model for investigating the influence of an external factor impairing the epithelial tissue such as an anticancer agent and radiation, on the epithelial tissue.

In addition, the three-dimensional structure prepared by a scaffold such as a collagen gel containing the cell having the ability to form the stratified epithelial tissue and the skin fibroblast can be used as a tool for determining and analyzing the drug efficacy of the test substance on the epithelial tissue. That is, the test substance is administered to the three-dimensional structure prepared by a scaffold such as a collagen gel containing the cell having the ability to form the stratified epithelial tissue and the skin fibroblast, and the drug efficacy of the test substance on the epithelial tissue is determined and analyzed, and thereby the drug efficacy of the test substance on the epithelial tissue can be determined and analyzed. Herein, the test substance means a substance to be subjected to determination and analysis for the drug efficacy on the epithelial tissue, and specifically it is exemplified by a candidate substance for a therapeutic drug for epithelial diseases. In particular, the stratified epithelial-formable cell induced from a relatively low invasive and collectable somatic cell such as peripheral blood circulating mononuclear cells is used, so that the drug efficacy on many donors having various genetic backgrounds can be broadly determined and analyzed.

In addition, the cell having the ability to form the stratified epithelial tissue can be used as a tool for clarifying and analyzing the pathological conditions of various epithelial tissues, and furthermore the cell having the ability to form the stratified epithelial tissue induced from a human somatic cell is useful as a tool for drug discovery and drug development for epithelial diseases. For example, a cell having the ability to form a stratified epithelial tissue can be produced by transducing a transgene into a somatic cell taken from a human body, and furthermore, by administering a test substance to an epithelium-like tissue prepared by culturing such a cell, drug efficacy of the test substance on the epithelium-like tissue can be determined and analyzed, and a stress on the epithelium-like tissue can be determined and analyzed by loading a stress such as an anticancer agent or radiation. Determination and analysis of the drug efficacy or the stress may be confirmed, e.g. by comparing a tissue to which the test substance has been administered or a tissue to which the stress has been added with a tissue without the test substance and the stress.

In addition, since the cell having the ability to form the stratified epithelial tissue has properties of a precursor cell or a stem cell such as self-replication ability and terminal differentiation, the cell can be used as a research tool for clarifying the properties of the stem cell by analyzing the process of transformation from the somatic cell such as skin fibroblast without this property to the cell having the ability to form the stratified epithelial tissue.

In addition, many of the so-called cancers have their origins in stratified epithelial tissues (squamous cancer), and the cell having the ability to form the stratified epithelial tissue can be used as a tool for cancer research.

2. Technique of Determining a Candidate for the Transgene

Hereinafter, the present invention will be described in detail on the basis of Examples and the like, but the present invention is not limited to them.

A skin fibroblast was selected as a representative of the somatic cell, and a keratinocyte was selected as a representative of the cell having the ability to form the stratified epithelial tissue. In order to select a candidate factor which can cause a direct conversion, a result of a microarray of expressed genes in a cultured human keratinocyte and a cultured human skin fibroblast was obtained from a database (Accession: GDS1505, ID: 1505) provided by NCBI in U.S. (FIG. 1).

Figure 2:
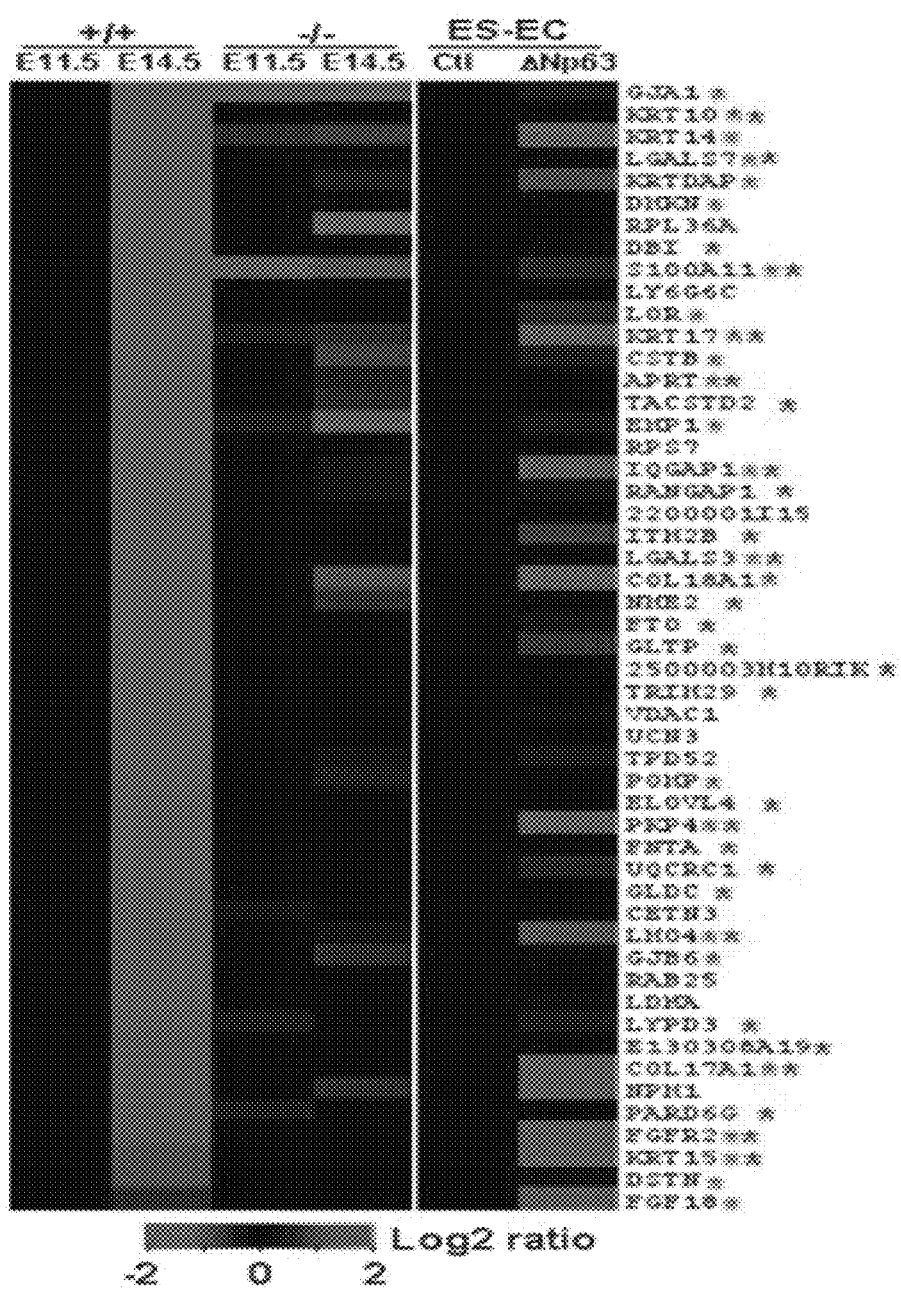
FIG. 2 illustrates a view showing data obtained by evaluating mRNA expressions in a mouse at the 11.5th fetal day and the 14.5th fetal day before and after development of its epidermis respectively using a microarray, in a form of heat map. The view shows the difference in expression genes between the case that a ΔNP63 gene considered to be important for epidermis development is knocked out and the case that it is not so. The figure is quoted from Citation 1.

Data in which mRNA expressions in a mouse at the 11.5th fetal day and the 14.5th fetal day before and after development of its epidermis respectively were evaluated by a microarray was obtained from Citation 1 (FIG. 2).

In order to further obtain data having a higher quantitative capability, microarray analysis was performed on a primary cultured fibroblast and a primary cultured keratinocyte separated from the same human skin specimen.

Separation and culture of the primary cultured fibroblast were carried out according to the method described in Citation 2. Specifically, a collected skin specimen was treated with 0.25% trypsin at 4° C. overnight, its epidermis is exfoliated, then explanted on a dish, to which a small amount of fibroblast growth medium (FGM) was added, left until the fibroblast migrated from the skin specimen to the dish, and passaged when the state became subconfluent.

Primary cultured keratinocyte was separated and cultured according to the method described in Citation 3. Specifically, a collected skin specimen was treated with 0.25% trypsin at 4° C. overnight, its dermis was scraped in a serum-free keratinocyte medium (SFKGM), and the keratinocyte remaining on the dermis was collected. The culture was continued in the SFKGM medium, and passaged when the state became subconfluent.

Figure 3:
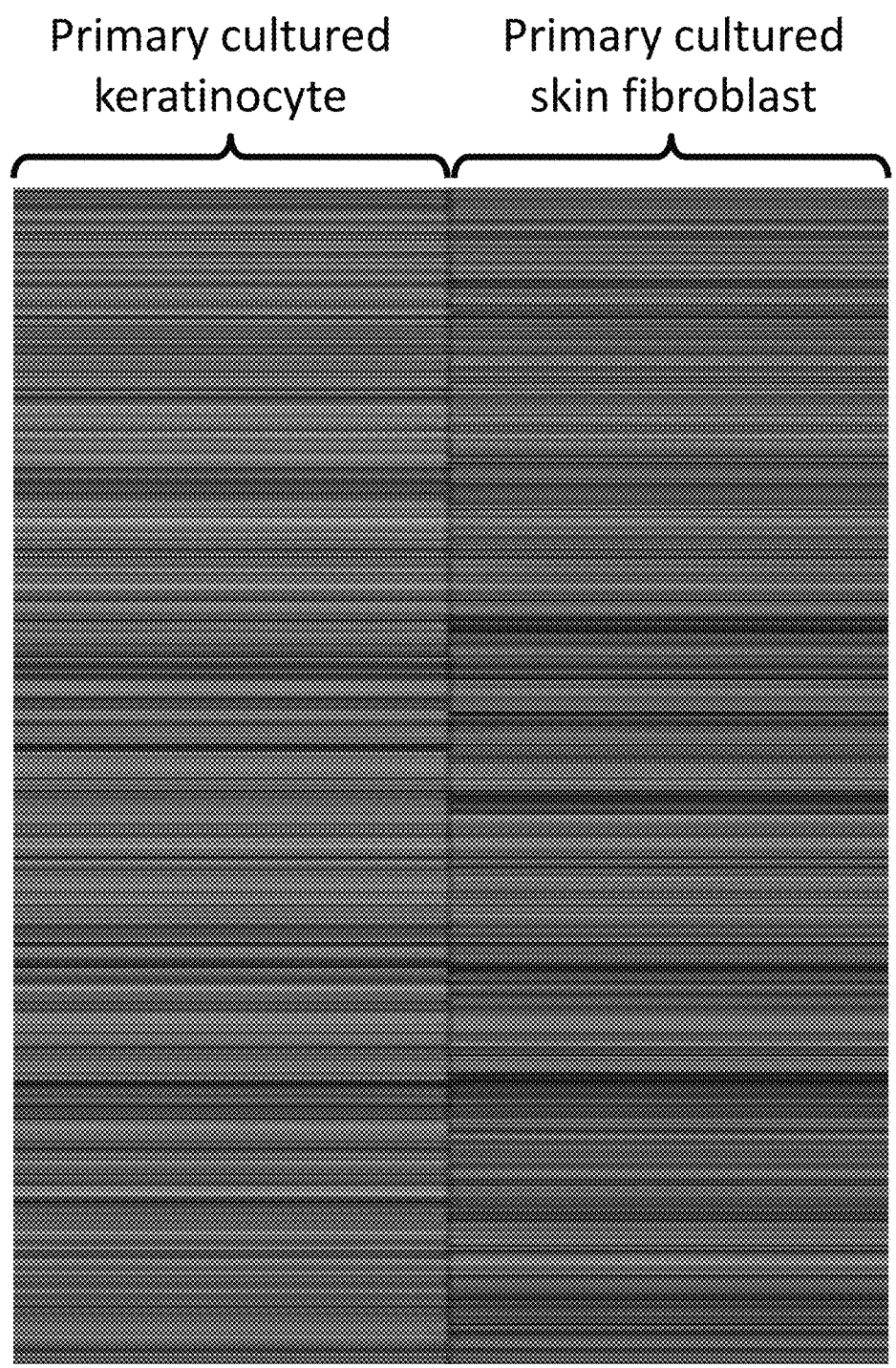
FIG. 3 illustrates a view showing data obtained by evaluating mRNAs of a primary cultured keratinocyte and a primary cultured skin fibroblast established from the same skin specimen by a microarray, in a form of heat map.

The total RNA was collected from $10^7$ cells of each of the primary cultured skin fibroblasts and the primary cultured keratinocytes, and their mRNA expressions were comprehensively compared with each other using Gene ST 1.0 microarray (Affymetrix, Inc.) (FIG. 3).

Figure 4:
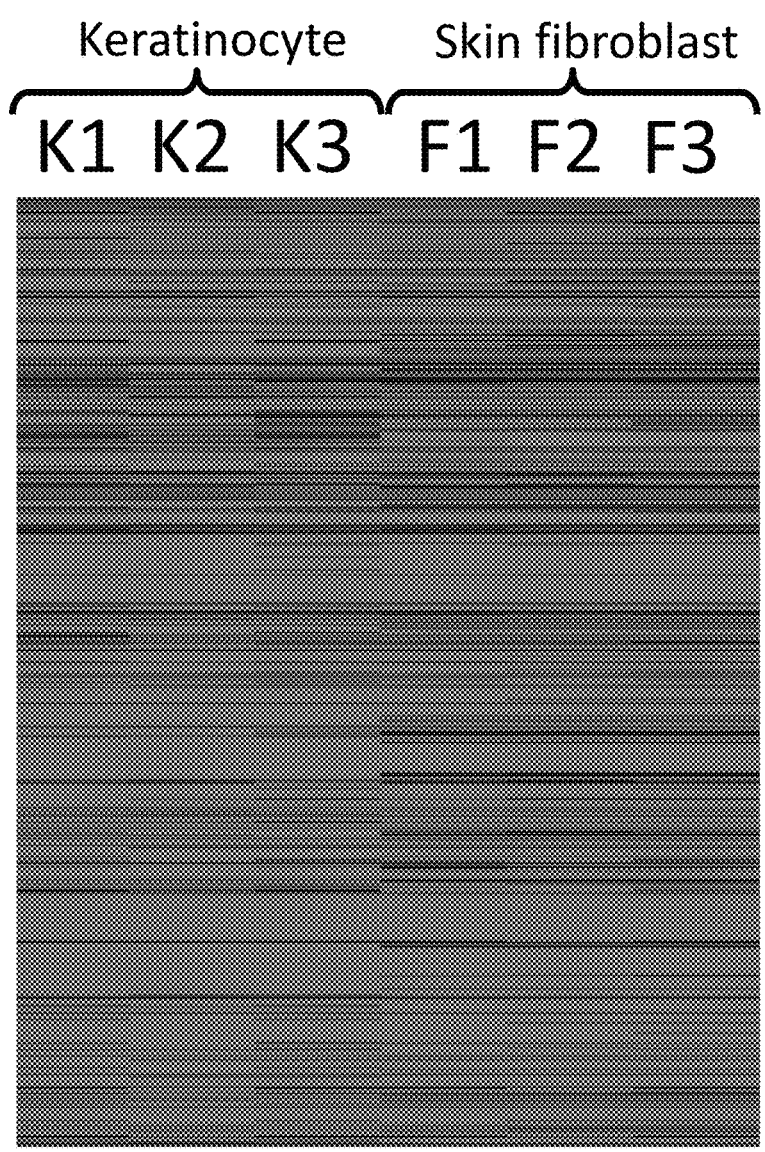
FIG. 4 illustrates a view showing data obtained by evaluating an expressed microRNA amount after a primary cultured fibroblast and a primary cultured keratinocyte were separated and cultured from three skin specimens of different sites collected from the same donor, by a microRNA microarray, in a form of heat map.

In order to compare the microRNAs expressing the primary cultured fibroblast, and the primary cultured keratinocyte, the primary cultured fibroblast and the primary cultured keratinocyte were separated and cultured from 3 skin specimens of different sites collected from the same donor, the microRNA was collected from $10^7$ cells, and the microRNA expressions were comprehensively compared using SurePrint G3 Human miRNA microarray (Agilent Technologies, Inc.) which is a microRNA microarray (FIG. 4).

It was confirmed from the above analysis that at least TFAP2A gene, TFAP2C gene, GRHL family genes, BNC1 gene, MYC family genes, GATA3 gene, OVOL1 gene, OVOL2 gene, ESRP1 gene, ESRP2 gene, GRHL1 gene, GRHL2 gene, GRHL3 gene, TP63 gene, DNP63A gene, MAPK13 gene, ARNTL2 gene, LASS3 gene, EHF gene, ZNF165 gene, ZNF750 gene, ZBED2 gene, IRX4 gene, SOX7 gene, SOX9 gene, FOXQ1 gene, PPP1R13L gene, KLF4 gene, hsa-mir-182, hsa-mir-183, hsa-mir-96, hsa-mir-200b, hsa-mir-200a, hsa-mir-429, hsa-mir-200c, hsa-mir-141, hsa-mir-203, hsa-mir-205, hsa-mir-135b, hsa-mir-17, hsa-mir-18a, hsa-mir-19a, hsa-mir-19b-1, hsa-mir-20a, hsa-mir-92a-1, and hsa-mir-367 are the genes relatively strongly expressed in the keratinocyte.

3. [Example 1] Induction from the Skin Fibroblast to the Cell Having the Ability to Form the Stratified Epithelial Tissue Based on the above analysis results, 27 transgenes listed in Table 2 were selected to prepare lentiviral vectors for transduction into the somatic cell. Table 2 shows the details of transcription factors selected as candidates, microRNAs, and lentiviral vectors prepared for forced expression and suppressed expression. In relation to the PPP1R13L gene, a vector was prepared for each of the two transcript variants.

TABLE 2

| Gene | Accession No. | Clone ID/ ProductID | Distributor | Backbone of Vector | Distributor |
| --- | --- | --- | --- | --- | --- |
| GATA3 | BC006793.1 | FLJ83421AAAN | NBRC | pLenti7.3/V5-DEST Gateway ® | Invitrogen |
| OVOL1 | BC059408.1 | FLJ84200AAAF | NBRC | pLenti7.3/V5-DEST Gateway ® | Invitrogen |
| OVOL2 | AK022284 | FLJ12222AAAN | NBRC | pLenti7.3/V5-DEST Gateway ® | Invitrogen |

TABLE 2-continued

| Gene | Accession No. | Clone ID/ ProductID | Distributor | Backbone of Vector | Distributor |
|---|---|---|---|---|---|
| ESRP1 | AK000178 | FLJ20171AAAN | NBRC | pLenti7.3/V5-DEST Gateway ® | Invitrogen |
| GRHL1 | AK312950 | FLJ93406AAAF | NBRC | pLenti7.3/V5-DEST Gateway ® | Invitrogen |
| GRHL2 | AK023844 | FLJ13782AAAN | NBRC | pLenti7.3/V5-DEST Gateway ® | Invitrogen |
| GRHL3 | AK315164 | FLJ96138AAAF | NBRC | pLenti7.3/V5-DEST Gateway ® | Invitrogen |
| TFAP2A | BC017754.1 | FLJ83504AAAF | NBRC | pLenti7.3/V5-DEST Gateway ® | Invitrogen |
| TP63 | BC039815.1 | FLJ84054AAAF | NBRC | pLenti7.3/V5-DEST Gateway ® | Invitrogen |
| DNP63A | AF075431 | EX-Z5740-LV215 | Gene Copoeia | pEZ-Lv215 | Gene Copoeia |
| MAPK13 | BC004428.1 | FLJ80046AAAN | NBRC | pLenti7.3/V5-DEST Gateway ® | Invitrogen |
| ARNTL2 | BC000172.3 | FLJ82905AAAF | NBRC | pLenti7.3/V5-DEST Gateway ® | Invitrogen |
| BNC1 | NM_001717 | EX-Z4401-Lv215 | Gene Copoeia | pEZ-Lv215 | Gene Copoeia |
| LASS3 | BC027616.2 | FLJ82453WAAF | NBRC | pLenti7.3/V5-DEST Gateway ® | Invitrogen |
| EHF | BC038995.2 | FLJ83365AAAF | NBRC | pLenti7.3/V5-DEST Gateway ® | Invitrogen |
| ZNF165 | BC026092.1 | FLJ82068AAAF | NBRC | pLenti7.3/V5-DEST Gateway ® | Invitrogen |
| ZNF750 | AK023903 | FLJ13841AAAN | NBRC | pLenti7.3/V5-DEST Gateway ® | Invitrogen |
| ZBED2 | BC003536.1 | FLJ80982AAAF | NBRC | pLenti7.3/V5-DEST Gateway ® | Invitrogen |
| ID1 | BC012420.1 | FLJ85176AAAF | NBRC | pLenti7.3/V5-DEST Gateway ® | Invitrogen |
| IRX2 | BC065189.1 | FLJ82376AAAN | NBRC | pLenti7.3/V5-DEST Gateway ® | Invitrogen |
| IRX4 | NM_016358 | EX-U0775-Lv201 | Gene Copoeia | pEZ-Lv201 | Gene Copoeia |
| SOX7 | AK055556 | FLJ30994AAAN | NBRC | pLenti7.3/V5-DEST Gateway ® | Invitrogen |
| SOX9 | NM_000346 | EX-M0312-Lv215 | Gene Copoeia | pEZ-Lv215 | Gene Copoeia |
| KLF4 | AK313489 | FLJ94042AAAN | NBRC | pLenti7.3/V5-DEST Gateway ® | Invitrogen |
| c-MYC | AK312883 | FLJ93327AAAN | NBRC | pLenti7.3/V5-DEST Gateway ® | Invitrogen |
| FOXQ1 | NM_033260 | Ex-Y5225-Lv214 | Gene Copoeia | pReceiver-Lv204 | Gene Copoeia |
| PPP1R13L | AK130326 | FLJ26816AAAN | NBRC | pLenti7.3/V5-DEST Gateway ® | Invitrogen |
| PPP1R13L | BC064913.1 | FLJ84348AAAF | NBRC | pLenti7.3/V5-DEST Gateway ® | Invitrogen |

For the lentiviral vector, a human Gateway entry clone was purchased from NBRC (National Institute of Technology and Evaluation, Biotechnology Department) if there was an appropriate clone, and the clone was subcloned to a pLenti 7.3/V5-DEST Gateway Vector (Life technologies, Inc.) according to a conventional method. Others were purchased from manufacturers (System Biosciences, Inc., GeneCopoeia, Inc., OriGene Technologies, Inc.).

A virus was prepared in order to transfect the lentiviral vector as a candidate factor for direct conversion in Table 1 into a skin fibroblast. For the virus preparation, ViraPower® HiPerform® Lentiviral Expression Systems (Life technologies, Inc.) were used. For the virus preparation, 10⁶ 293FT cells were seeded on each well of a 6 well plate, and left overnight, then the medium in each well was exchanged with Opti-MEM Reduced Serum Medium, GlutaMAX® Supplement (Life technologies, Inc.) supplemented with 1 mL of 10% FBS, and then gene transduction was carried out using 600 ng of the construct, 1.2 µg of ViraPower® Lentiviral Packaging Mix and 7.2 µl of Lipofectamine 2000. After 24 hours, the medium was exchanged with 2 ml of 293FT cell growth medium, and after further 48 hours, the medium containing the virus solution was recovered. After centrifuging the virus-containing medium, the supernatant was recovered, to which a quarter amount of PEG-it Virus Precipitation Solution (System Biosciences, Inc.) was added, and the mixture was allowed to stand at 4° C. overnight. Centrifugation was carried out at 1500×G, the supernatant was discarded, and the precipitate was pipetted with 20 µl of PBS to obtain a virus concentrate. The virus solution recovered by the aforementioned operation was used as one unit for gene transduction into a skin fibroblast.

For gene transduction into the skin fibroblast, Transdux® (System Biosciences, Inc.) was used. 24 hours before transduction, 6000 skin fibroblasts were seeded per well in a 48-well plate. The medium was exchanged with 300 µl of fibroblast growth medium containing the virus solution, and centrifuged at 800×G for 30 minutes. Again, the medium was exchanged with 300 µl of fibroblast growth medium containing a new virus solution, centrifuged at 800×G for 30 minutes, and then the inside of the well was washed with PBS, to which 300 μl of fibroblast growth medium was added.

Figure 5:
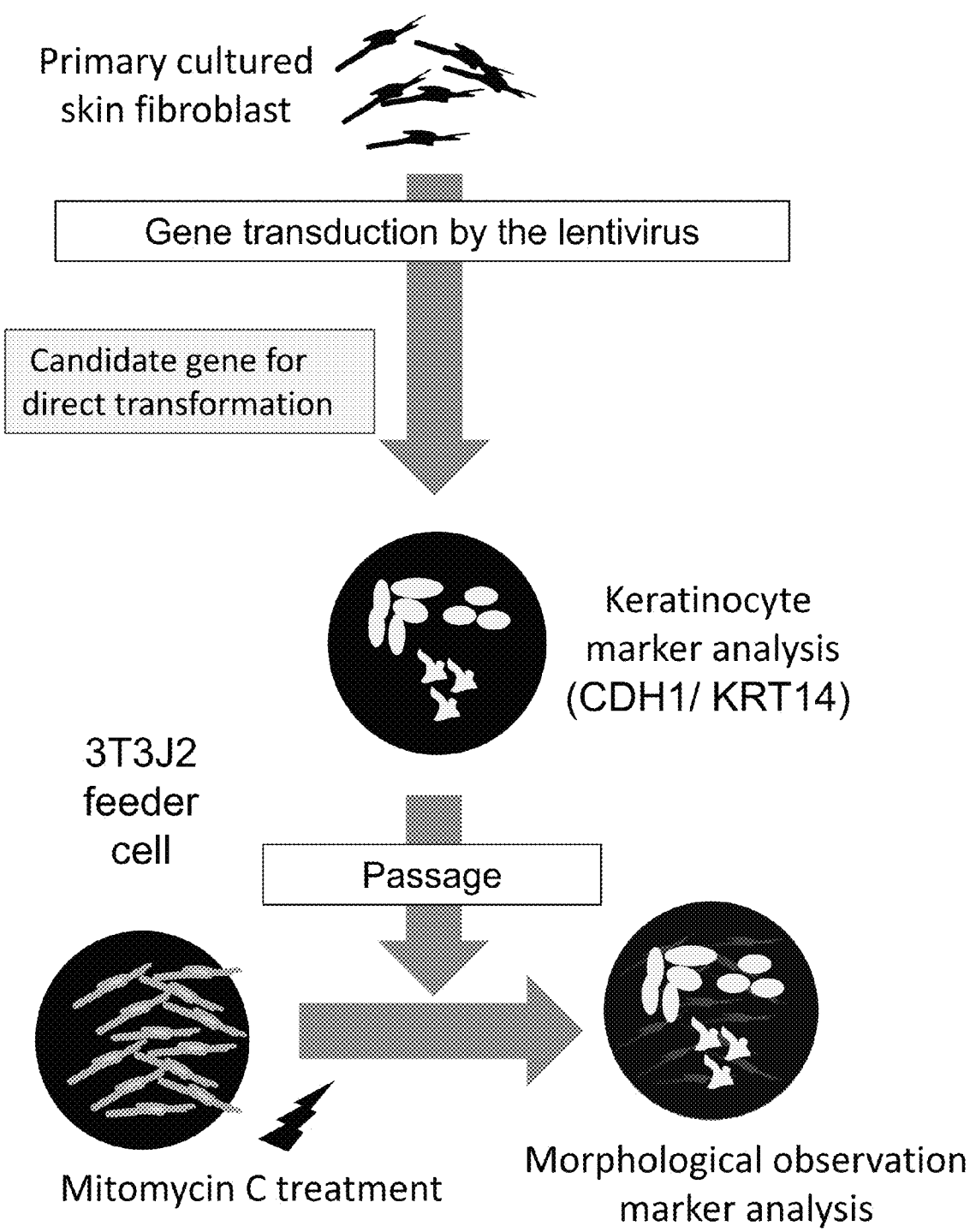
FIG. 5 illustrates a schema of a gene transduction test. The schema shows that a candidate gene for transformation is directly transduced into a skin fibroblast using a lentivirus and passaged on a 3T3J2 feeder cell treated with mitomycin C, and then the presence or absence of transformation into a cell having the ability to form a stratified epithelial tissue is observed.
Figure 6:
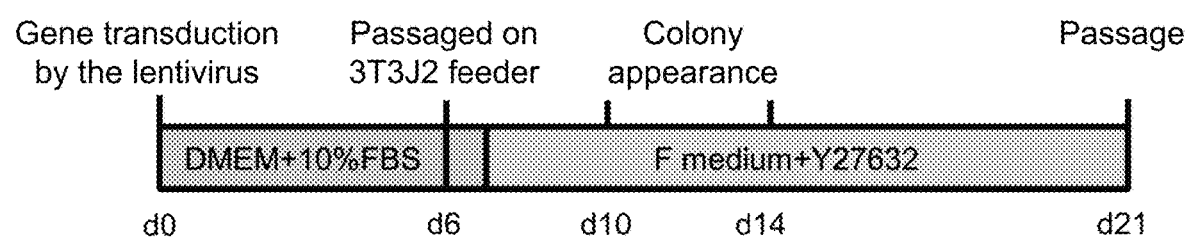
FIG. 6 illustrates a time course of the gene transduction test. The diagram shows that the cell is passaged on the 6th day after the gene transduction, and the culture is continued in a keratinocyte F medium containing Y27632 which is an Rho kinase inhibitor, on a feeder.

For the cell after the gene transduction, the medium was exchanged with the fibroblast growth medium on day 1, day 2 and day 4 of the transduction, and on day 6, the cell was passaged on a 3T3-J2 feeder cell prepared in the 6-well plate treated with mitomycin using the fibroblast growth medium. On day 2 of the passage, the medium was replaced with a keratinocyte F medium containing Y27632 (Wako Pure Chemical Industries, Ltd.) which is an Rho-kinase inhibitor, and thereafter the medium was exchanged every 2 days (FIGS. 5 and 6).

The 3T3-J2 feeder cell used as a feeder is a cell line obtained from JTEC CORPORATION. Using the 3T3 cell medium prepared by adding 10% bovine neonatal serum to a DMEM medium, the cell was maintained according to a conventional method, furthermore the cell was treated in a medium containing 10 μg/ml of mitomycin C for one hour on the day before used as a feeder cell, then passaged at a concentration of $2.0 \times 10^5$ cells/well, and used as a feeder.

Figure 7:
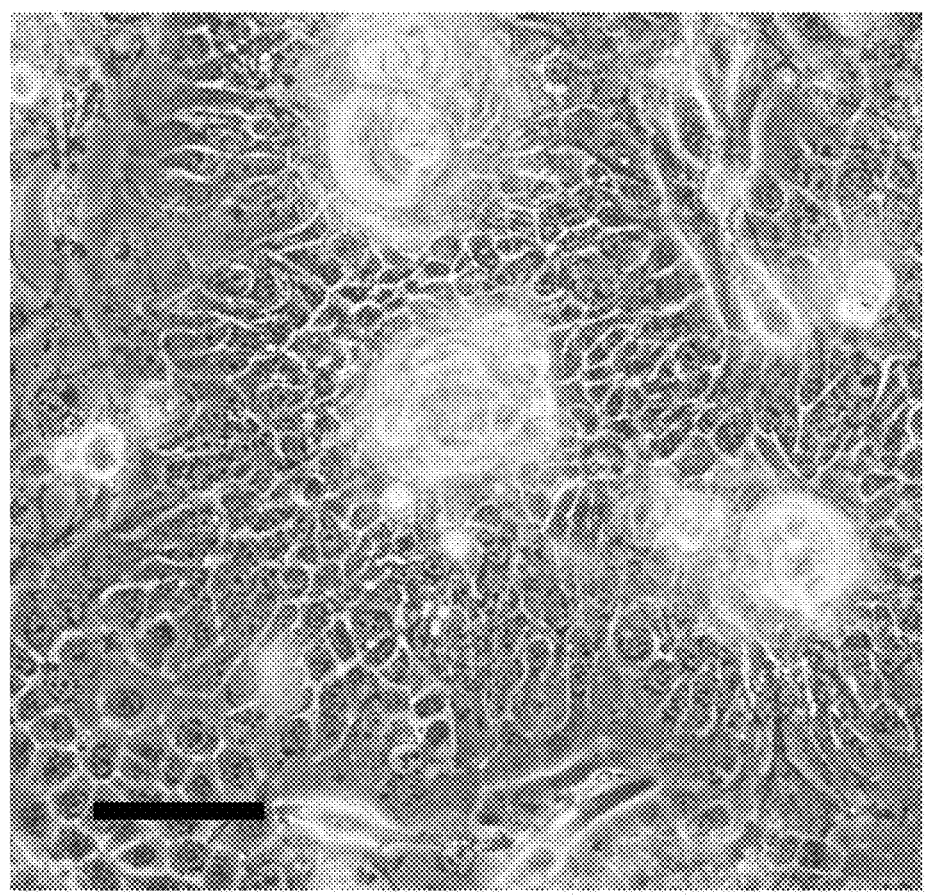
FIG. 7 illustrates a view of a primary cultured keratinocyte cultured in the keratinocyte F medium containing an Rho kinase inhibitor Y27632, on a 3T3J2 feeder cell.

The keratinocyte F medium was prepared according to a conventional method. In this test, 2.5 ml of FBS was added to a mixture of 33.8 ml of F12 medium (Life technologies, Inc.) and 11.2 ml of high glucose DMEM (Life technologies, Inc.), and adjusted so as to have a constitution of 24 μg/ml of adenine (Sigma-Aldrich Co. LLC.), 8.4 ng/ml of cholera toxin (Wako Pure ChemicalIndustries, Ltd.), 5 μg/ml of insulin, 0.4 μg/ml of hydrocortisone (Sigma-Aldrich Co. LLC.), 100 U/ml of penicillin (Sigma-Aldrich Co. LLC.), 100 μg/ml of streptomycin (Sigma-Aldrich Co. LLC.) and 10 ng/ml of EGF. Furthermore, in this test, according to the point that the lifetime of cultured keratinocyte can be prolonged by adding an Rho-kinase inhibitor (Y27632) to the medium in the presence of the 3T3 feeder cell (Citation 4), the keratinocyte F medium was adjusted so as to contain 10 μM of Y-27632 (Wako Pure ChemicalIndustries, Ltd.) for use. In addition, the primary cultured keratinocytes were cultured under the same conditions for comparison (FIG. 7).

Figure 8:
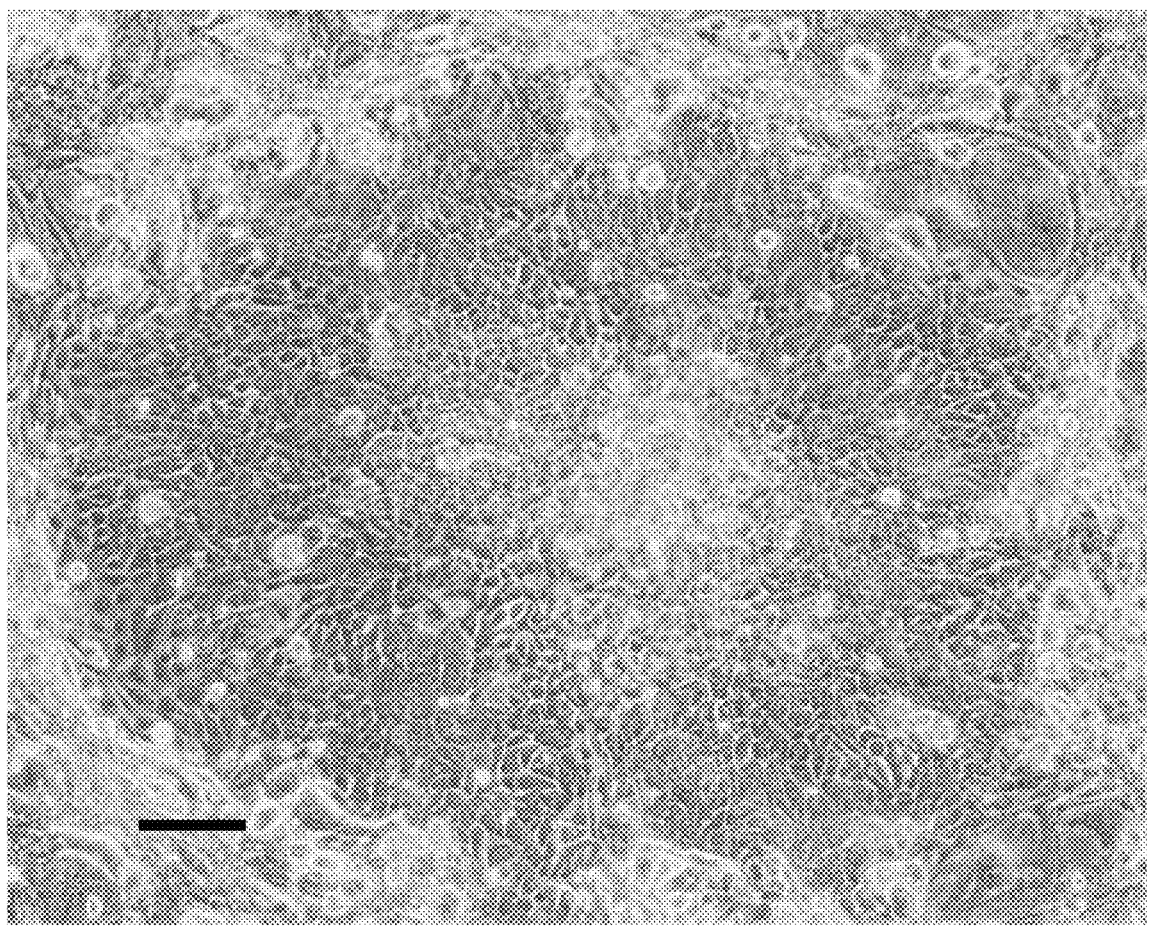
FIG. 8 illustrates a view of colonies of an induced fibroblast prepared by transfecting GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene with a KRT14-RFP reporter. The colony shows a morphology similar to that of the keratinocyte colony having a distinct boundary with the surrounding feeder and the uninduced cells, in which flat cells are located on the margin of the colony and overlap towards the center.

The transduced fibroblast to which the 27 genes (GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene) in Example 1 were transduced provided a cell exhibiting colonies with proliferation and morphology similar to those of the keratinocyte (FIG. 8). In FIG. 8, the colony has distinct boundaries with the surrounding feeder and the uninduced cells, and flat cells are located on the margin of the colony and overlap toward the center, and show the morphology similar to that of the colony of the keratinocyte in FIG. 7.

Figure 9:
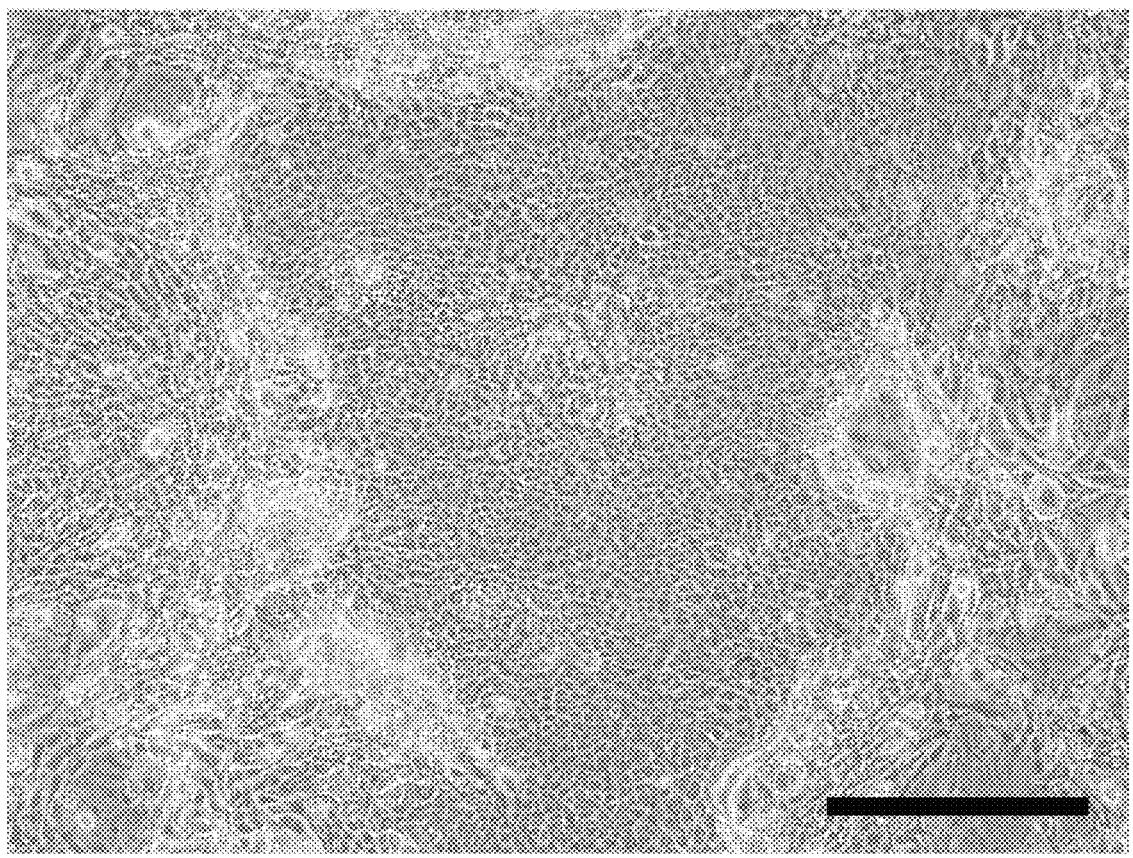
FIG. 9 illustrates a view of a second-passage colony after confirming the colonies of an induced fibroblast prepared by transfecting GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene with a KRT14-RFP reporter.

The cell could be passaged and proliferated while maintaining the proliferation and morphology similar to those of the keratinocyte in a culture environment on the 3T3-J2 feeder cells considered to selectively proliferate the keratinocyte, even in the absence of special cell separation (FIG. 9). FIG. 9 is a view of the second-passage colony which was passaged after confirming the colony of the induced fibroblast in FIG. 8. From FIG. 9, it was confirmed that the purity of the induced fibroblast was increased by the passage operation, because the induced fibroblast in Example 1 shows a relatively high proliferative potency compared to the uninduced fibroblast not induced to a state similar to the keratinocyte under the culture condition. Incidentally, an induced fibroblast with high purity can be obtained in a shorter time by selectively extracting and subculturing a colony similar to the keratinocyte in the induced fibroblasts in FIG. 8.

Figure 10:
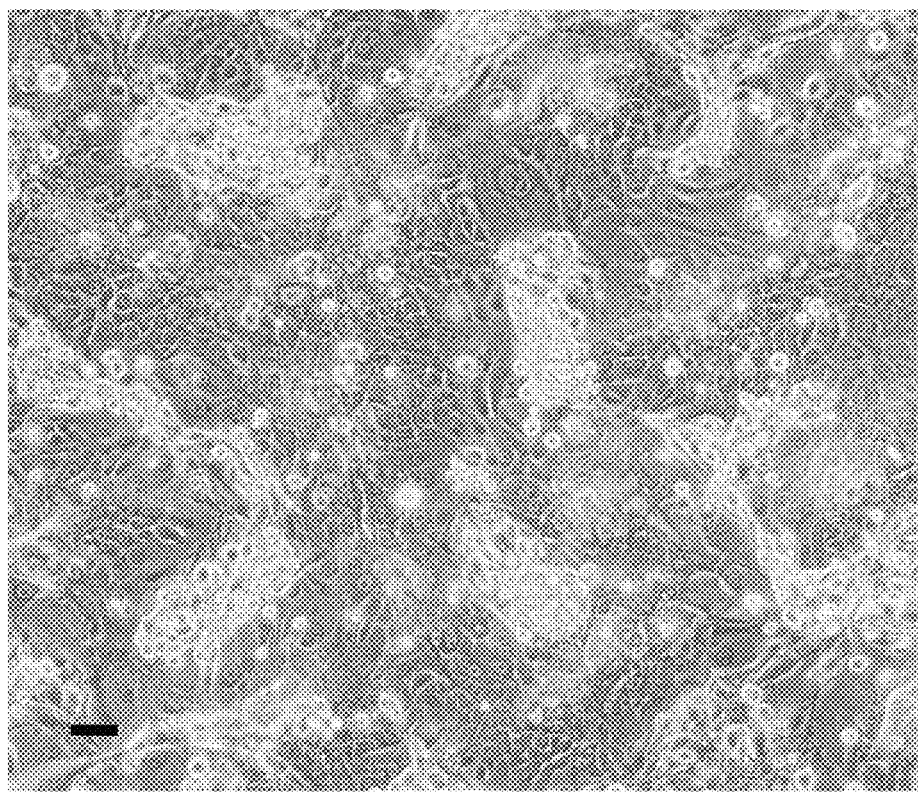
FIG. 10 illustrates views of cells separated using a label with an anti-Epi-CAM antibody in the second-passage colony after confirming the colonies of an induced fibroblast prepared by transfecting GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene with a KRT14-RFP reporter (the upper view). The view shows that the cell expresses an epithelial marker Epi-CAM. Furthermore, it shows that red fluorescence resulting from the KRT14-RFP reporter can be confirmed, and the cell is KRT14 positive (the lower view).
Figure 10:
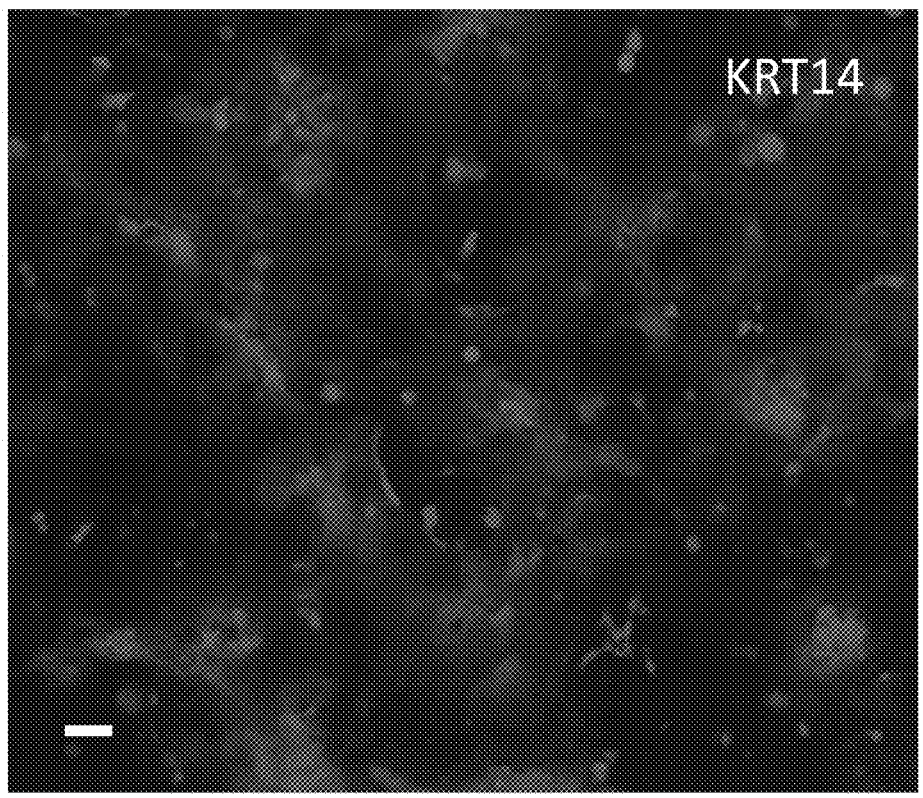

In addition, magnetic cell separation was carried out using a magnetic labeled antibody against Epi-CAM which was a general epithelial cell marker, and it was confirmed that the cell showed colonies having systematized proliferation and morphology more similar to those of the keratinocyte (FIG. 10, the upper view). The upper view of FIG. 10 is a view of the cell obtained by separating the cell using labeling with anti-Epi-CAM antibody at the second passage after confirming the colony of the induced fibroblast in FIG. 8. Furthermore, it was also confirmed that KRT14 was expressed by the simultaneously-transduced KRT14-RFP reporter (pRZ-hKeratin (Cat # SR900CS-1, System Biosciences, Inc.) (FIG. 10, the lower view). The magnetic cell separation by the magnetic labeled anti-Epi-CAM antibody was carried out using CD326 (EpCAM) microbeads, human (Miltenyi Biotec K.K.) as a labeled antibody, by means of a manual cell separator, MACS cell separation column (Miltenyi Biotec K.K.).

Figure 11:
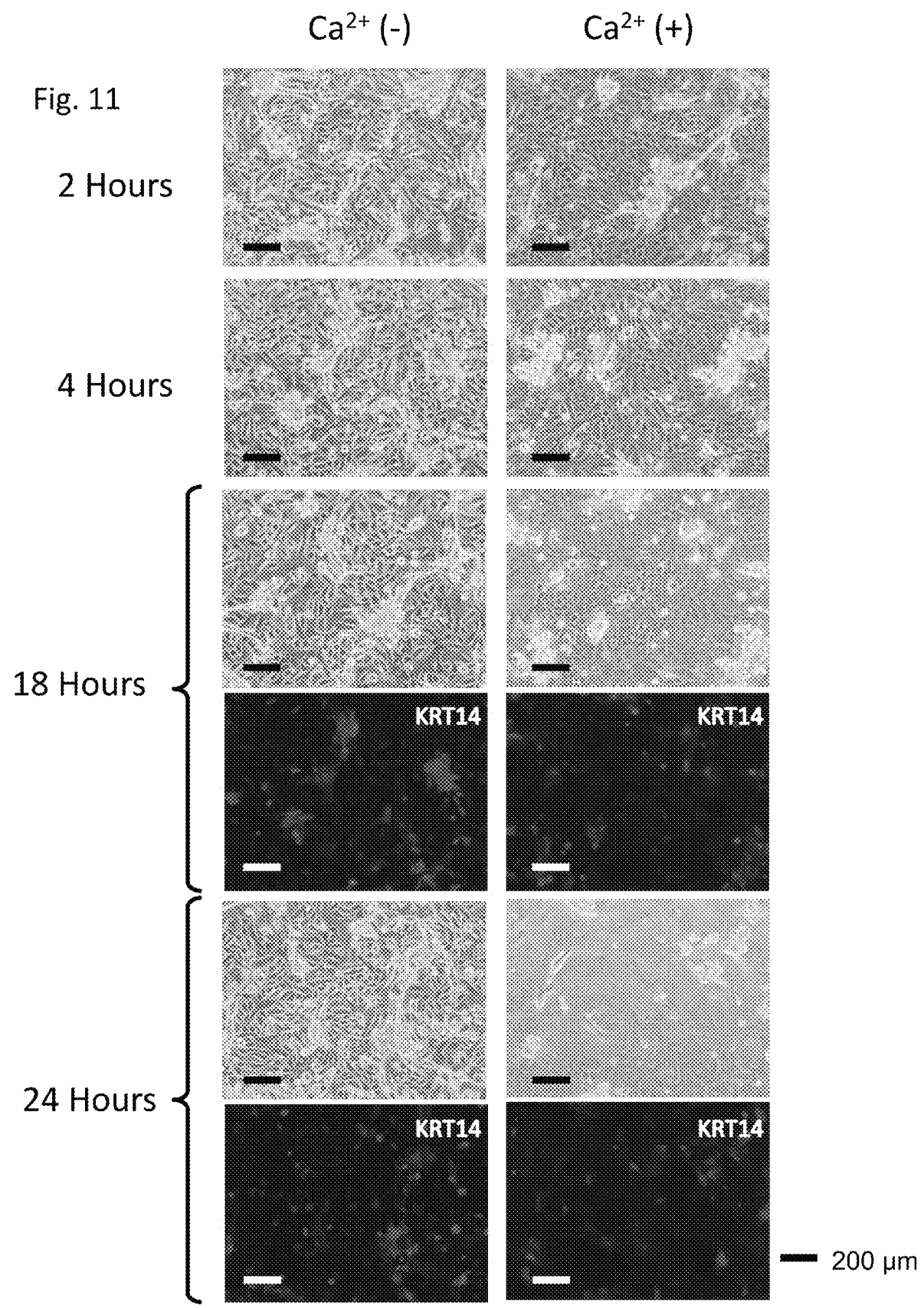
FIG. 11 illustrates a time-dependent change when 1.8 mM of $Ca^{2+}$ was added to the induced fibroblast on monolayer culture. The left column indicates a culture without $Ca^{2+}$. The right column indicates a culture with $Ca^{2+}$. The views explain that terminal differentiation of the induced fibroblast is initiated by addition of $Ca^{2+}$ and the cell bodies are flatly broadened. Also, the views explain that the expression of KRT14 is decreased by addition of $Ca^{2+}$.

Furthermore, after separating the cell using the anti-Epi-CAM antibody, the culture was continued, the induced fibroblast passaged and amplified was passaged with a serum-free keratinocyte medium in a monolayer culture condition, and the culture was continued for 8 days, the induced fibroblast was accustomed to the serum-free keratinocyte medium, and then the medium was exchanged with a serum-free keratinocyte medium with a $Ca^{2+}$ concentration adjusted to 1.8 mM. It was observed that the cell was flattened and spread over time (FIG. 11). In FIG. 11, the left column shows the state without addition of $Ca^{2+}$, the right column shows the state with addition of $Ca^{2+}$, and for the time courses in 18 hours and 24 hours, the red fluorescence states resulting from the KRT14-RFP reporter are also shown. From the left and right views, it can be confirmed that the induced fibroblast starts terminal differentiation by addition of $Ca^{2+}$, and the cell body is flatly spread. Furthermore, from the views of the red fluorescence states, it was observed that the KRT14 expression concomitantly decreased. These views show the same terminal differentiative potency as that observed when $Ca^{2+}$ is added to the keratinocyte, indicating that the induced skin fibroblast under the monolayer culture condition has the same terminal differentiative potency as of the keratinocyte.

Figure 12:
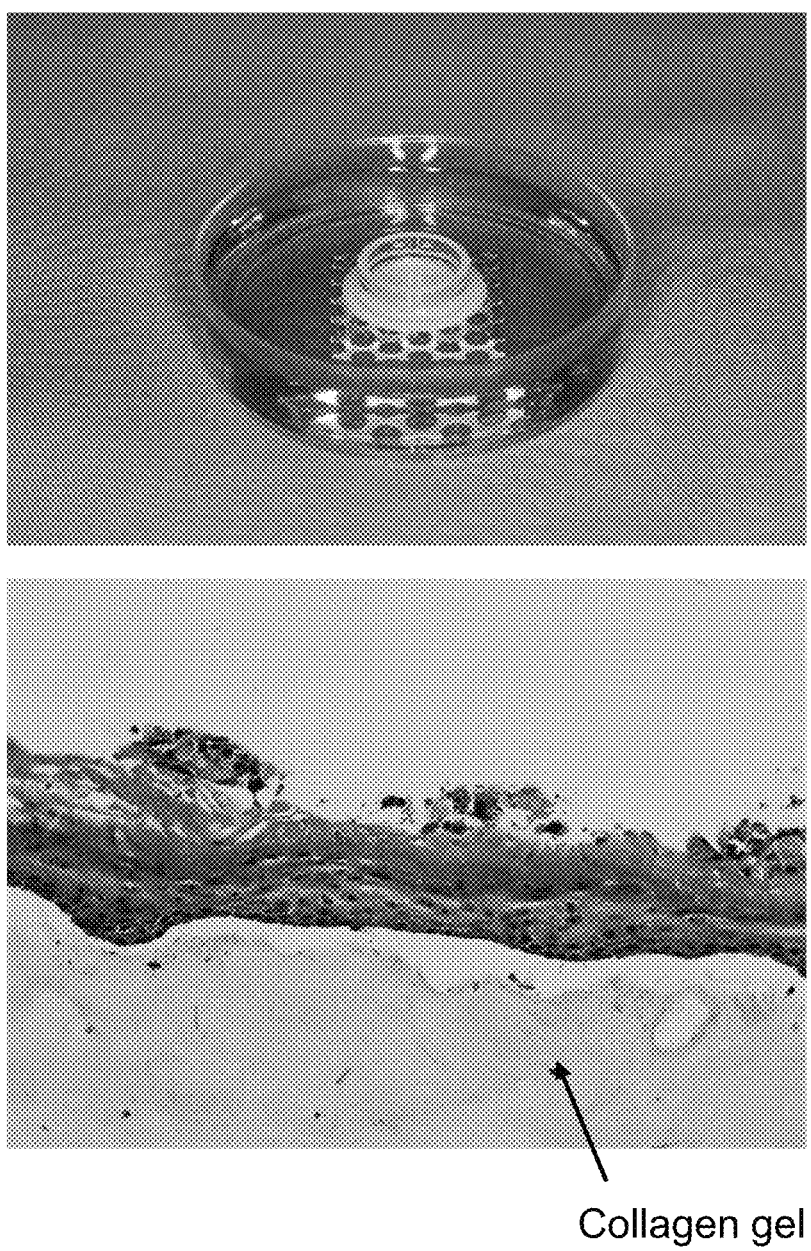
FIG. 12 illustrates a view showing that the induced fibroblast forms a stratified keratinized epithelium on a gas-liquid interface by a three-dimensional culture. The upper view shows an image of an appearance during the three-dimensional culture. The lower view shows a histological finding of the stratified epithelium-like tissue composed of a collagen gel and the induced fibroblast after the three-dimensional culture. The induced fibroblast forms the stratified epithelium-like tissue on the collagen gel by the three-dimensional culture, and a keratinized layer is also recognized in a more upper layer.

After separating the cell using the anti-Epi-CAM antibody, the culture was continued, the induced fibroblast passaged and amplified was used to culture the cell on a collagen gel containing the skin fibroblast, and the epithelial tissue-forming ability was tested by means of a three-dimensional skin culture model for investigating the epithelial tissue forming ability by exposing the cell to a gas-liquid interface, and it was confirmed that the induced fibroblast had the stratified epithelial tissue-forming ability under the aforementioned condition (FIG. 12).

The three-dimensional skin culture model was prepared using the methods of Citations 5 and 6. Specifically, to 3 ml of a collagen acidic solution I-PC 5 mg/mL (KOKEN CO., LTD.), Hepes ph 7.4 and $NaHCO_3$ were added so that each of their final concentrations was 10 mM, then 4 ml of a DMEM medium supplemented with 10% FBS, containing $10^6$ fibroblasts was added, stirred, then transferred to a 6 cm dish, and allowed to stand in an incubator at 37° C. for 30 minutes. At the start of gelation, the dish was tapped to rise the gel from the surface of the dish. Since gel shrinkage started thereafter, the medium was exchanged every two days, and on day 7 to 10, the three-dimensional skin culture with the skin fibroblast was started.

The collagen gel containing the skin fibroblast obtained in such a way was placed on an aluminum support stand using a sterilized nylon mesh, and furthermore a glass cylinder with an inner diameter of 10 mm and an outer diameter of 12 mm was placed on the collagen gel as shown in the upper view of FIG. 12. Through these operations, the space inside of the glass cylinder was separated from the outside of the glass cylinder by the glass cylinder and the collagen gel. The outside of the glass cylinder was filled with a medium prepared by mixing the DMEM medium supplemented with 10% FBS and a serum-free keratinocyte medium at a ratio of 1:1, and in the inside of the glass cylinder, the induced fibroblasts in a subconfluent state was seeded in 1 well of the 6-well plate with 200 µl of SFKGM. Thereafter, the inner medium was exchanged with the serum-free keratinocyte medium every day, the outer medium was exchanged with a mixed medium of the DMEM medium supplemented with 10% FBS with a $Ca^{2+}$ concentration adjusted to 1.8 mM and the serum-free keratinocyte medium at a ratio of 1:1 every second day. From day 4, the inner medium was exhausted, the induced fibroblast was placed in an environment of the gas-liquid interface while the liquid level of the outer medium was conformed to the height of the collagen gel, and the culture was continued until day 14.

The lower view of FIG. 12 is a cross-sectional photograph of the induced fibroblast and the collagen gel after the three-dimensional culture, and it was confirmed that the stratified epithelium-like tissue was formed from the induced fibroblast on the collagen gel, and a keratinized layer was also formed in a more upper layer.

When a genomic DNA of the induced fibroblast prepared according to the aforementioned method was subjected to a PCR reaction using a primer specific to a viral vector-derived gene, it was confirmed that the 9 genes: OVOL1 gene, TFAP2A gene, GRHL2 gene, BNC1 gene, LASS3 gene, ZBED2 gene, SOX7 gene, SOX9 gene and c-MYC gene were inserted to the induced fibroblast. For confirming the inserted gene derived from the virus vector, PCR reactions using specific primers shown in Table 3 were carried out. For the PCR reaction, AccuPrime Pfx Supermix (Life technologies, Inc.) was used, and to 11.5 µl of AccuPrime Pfx Supermix reagent, a forward primer and a reverse primer were added per one reaction so that their final concentrations were 200 nM, to which 10 ng of Template DNA was added. After that, a hot start was carried out in a thermal cycler at 95° C. for 5 minutes, then a PCR product obtained by repeating the cycle of 95° C. for 15 seconds, 63° C. for 30 seconds and 68° C. for 60 seconds was repeated 35 cycles was electrophoresed with 1% of E-Gel® EX Gel (Invitrogen Corporation) using E-Gel® agarose gel electrophoresis system (Invitrogen Corporation) to confirm the presence of a target gene.

TABLE 3

| Gene | | Primer |
|---|---|---|
| GATA3 | Forward | CGCAAATGGGCGGTAGGCGTG |
| | Reverse | ACACCTGGCTCCCGTGGTG |
| OVOL1 | Forward | CGCAAATGGGCGGTAGGCGTG |
| | Reverse | CCCAGGCTGACTGGCACGTAGATC |
| OVOL2 | Forward | CGCAAATGGGCGGTAGGCGTG |
| | Reverse | CCTAGGCCCACTGGGATGTAGGTG |
| ESRP1 | Forward | CGCAAATGGGCGGTAGGCGTG |
| | Reverse | AGTGCTGCACCTCCCTTGGC |
| TFAP2A | Forward | CGCAAATGGGCGGTAGGCGTG |
| | Reverse | GAGTAAGGATCTTGCGACTGGGGG |
| ID1 | Forward | CGCAAATGGGCGGTAGGCGTG |
| | Reverse | GCGAGATGGCCACGCTCTGC |
| GRHL1 | Forward | CGCAAATGGGCGGTAGGCGTG |
| | Reverse | GCTTTGGTCGCTGCAGTGAGAGGG |
| GRHL2 | Forward | CGCAAATGGGCGGTAGGCGTG |
| | Reverse | GGCTGCTGTCAGGGGATTCTCC |
| GRHL3 | Forward | CGCAAATGGGCGGTAGGCGTG |
| | Reverse | CGCTTCTCCTTGGGACCCATGTAG |
| DNP63A | Forward | GGCCACCTGGACGTATTCCACTGAA |
| | Reverse | GAGGGGCAATCTGTCCCTCGTTG |
| TP63 | Forward | CGCAAATGGGCGGTAGGCGTG |
| | Reverse | ACTGTGGCCACATGGGGTCAC |
| MAPK13 | Forward | CGCAAATGGGCGGTAGGCGTG |
| | Reverse | CGATGGCCGAGCACACGGAG |
| ARNTL2 | Forward | CGCAAATGGGCGGTAGGCGTG |
| | Reverse | GGCTATGAGCTTCTTGGGATGGGTC |
| BNC1 | Forward | GCAGGATGGCCGAGGCTATCAG |
| | Reverse | GGACTGGACAATCTCCACCTGGC |
| LASS3 | Forward | CGCAAATGGGCGGTAGGCGTG |
| | Reverse | CAGTTTGCAATGGTTGCCTTGTGG |
| EHF | Forward | CGCAAATGGGCGGTAGGCGTG |
| | Reverse | CCAGGAGGTGCTGGAGCCAC |
| ZNF165 | Forward | CGCAAATGGGCGGTAGGCGTG |
| | Reverse | TGGCTTCAGCCACTGACAGCAG |
| ZNF750 | Forward | CGCAAATGGGCGGTAGGCGTG |
| | Reverse | GTGGCATCGGGCTGGTTGG |
| ZBED2 | Forward | CGCAAATGGGCGGTAGGCGTG |
| | Reverse | GGCAGGTGGCATACTGGTTGGG |
| IRX2 | Forward | CGCAAATGGGCGGTAGGCGTG |
| | Reverse | CGTAGGGTGCGCCCATGTAGG |
| IRX4 | Forward | CCTCGGCTCCCCAGTTCTTGAT |
| | Reverse | GCTGTTCAGCGAGTAGAAGGCGG |
| SOX7 | Forward | CGCAAATGGGCGGTAGGCGTG |
| | Reverse | CGACTTTCCCAGCATCTTGCTGAGC |
| SOX9 | Forward | CTCTGGAGACTTCTGAACGAGAGCG |
| | Reverse | CCCTGGGATTGCCCCGAGTG |
| SOX15 | Forward | CGCAAATGGGCGGTAGGCGTG |
| | Reverse | TTCTGCTGCGCCATCTGGC |
| FOXQ1 | Forward | GACCAGGGTAGAGCTCCCGG |
| | Reverse | CCCTCCAGGTCACTGCCCTG |
| PPP1R13L | Forward | CGCAAATGGGCGGTAGGCGTG |
| | Reverse | GGCGGCCTAGAAGGGGGTC |
| KLF4 | Forward | CGCAAATGGGCGGTAGGCGTG |
| | Reverse | GCTCTCCAGGTCTGTGGCCAC |
| MYC | Forward | CGCAAATGGGCGGTAGGCGTG |
| | Reverse | GAGAAGGGTGTGACCGCAACGTAG |

As can be understood from Example 1, the induction of the cell having the ability to form the stratified epithelial tissue does not require all of the 27 genes: GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, IRX2 gene, IRX4 gene, SOX7 gene, SOX9 gene, FOXQ1 gene, PPP1R13L gene, KLF4 gene and c-MYC gene, and the somatic cell is likely to be directly converted to the cell having the ability to form the stratified epithelial tissue by transducing at least 9 genes OVOL1 gene, TFAP2A gene, GRHL2 gene, BNC1 gene, LASS3 gene, ZBED2 gene, SOX7 gene, SOX9 gene, and c-MYC gene. Note that Example 1 means that the cell can be directly converted into the cell having the ability to form the stratified epithelial tissue by transducing all of such 9 genes, but does not mean that all of the 9 genes are indispensable for direct conversion. Also, in light of Example 2 described below, the cell can be directly converted into the cell having the ability to form the stratified epithelial tissue, even by transducing only some of the 9 genes.

Figure 13:
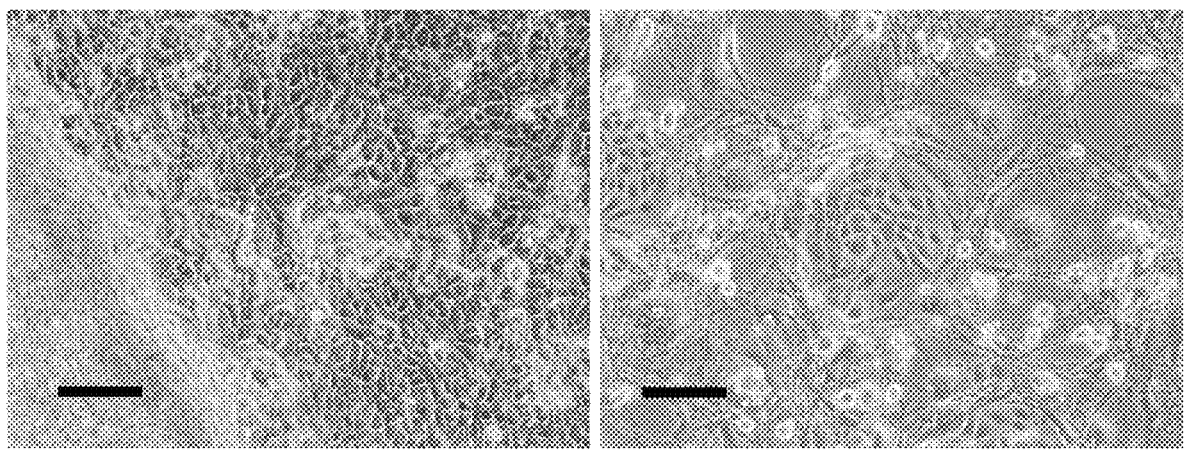
FIG. 13 illustrates colonies of cells in which insertions of GATA3 gene, TFAP2A gene, GRHL2 gene, TP63 gene, BNC1 gene, EHF gene, ZNF165 gene and c-MYC gene into a genomic DNA were confirmed. The left view shows a high-density area, and the right view shows a low-density area.

4. [Example 2] Induction from the Skin Fibroblast to the Cell Having the Ability to Form the Stratified Epithelial Tissue As transgenes, 25 genes which remained after eliminating 2 genes IRX2 gene and IRX4 gene from the 27 genes listed in Table 2 were transduced into the skin fibroblast. The basic experimental condition and experimental method are the same as in Example 1. In the same way as Example 1, 25 transgenes were transduced into the skin fibroblast to obtain an induced fibroblast cultured. FIG. 13 is a view showing colony of the induced fibroblast prepared according to the aforementioned method. The left view shows a high-density area, and the right view shows a low-density area. FIG. 13 indicates that the colony of the induced fibroblast in Example 2 has a distinct boundary with the surrounding feeder and the uninduced cells, and flat cells are located on the margin of the colony and overlap toward the center, and show the morphology similar to that of the colony of the keratinocyte in FIG. 7.

When the induced fibroblast of Example 2 was subjected to a PCR reaction using a primer specific to a viral vector-derived gene (Table 3) with respect to genomic DNA of, it was confirmed that the 8 genes: GATA3 gene, TFAP2A gene, GRHL2 gene, TP63 gene, BNC1 gene, EHF gene, ZNG165 gene and c-MYC gene were inserted. Although the cell into which such 8 genes were inserted exhibited proliferation and morphology similar to those of the keratinocytes, it exhibited high proliferative potency and low terminal differentiative potency compared to the cell into which 9 genes OVOL1 gene, TFAP2A gene, GRHL2 gene, BNC1 gene, LASS3 gene, ZBED2 gene, SOX7 gene, SOX9 gene and c-MYC gene were inserted in Example 1.

As can be understood from Example 2, the induction of the cell having the ability to form the stratified epithelial tissue does not require all of the 25 genes: GATA3 gene, OVOL1 gene, OVOL2 gene, ESRP1 gene, TFAP2A gene, ID1 gene, GRHL1 gene, GRHL2 gene, GRHL3 gene, TP63 gene, DNP63A gene, MAPK13 gene, ARNTL2 gene, BNC1 gene, LASS3 gene, EHF gene, ZNF165 gene, ZNF750 gene, ZBED2 gene, SOX7 gene, SOX9 gene, FOXQ1 gene, PPP1R13L gene, KLF4 gene and c-MYC gene, and the somatic cell is likely to be directly converted to the cell having the ability to form the stratified epithelial tissue by transducing at least 8 genes GATA3 gene, TFAP2A gene, GRHL2 gene, TP63 gene, BNC1 gene, EHF gene, ZNF165 gene, and c-MYC gene. Note that Example 2 means that the cell can be directly converted into the cell having the ability to form the stratified epithelial tissue by transducing all of such 8 genes, but does not mean that all of the 8 genes are indispensable for direct conversion.

According to Examples 1 and 2, in the cell having the ability to form the stratified epithelial tissue finally derived from the somatic cell, 4 genes TFAP2A gene, GRHL2 gene, BNC1 gene and c-MYC gene were confirmed commonly in both Example 1 and Example 2. Consequently, it is highly likely that the somatic cell can be directly converted to the cell having the ability to form the stratified epithelial tissue by transducing TFAP2A gene, GRHL2 gene, BNC1 gene and c-MYC gene. In addition, instead of or in combination with the TFAP2A gene, a TFAP2C gene having the same function may be transduced, or alternatively, instead of or in combination with the GRHL2 gene, the GRHL family genes may be transduced, or alternatively, instead of or in combination with the c-MYC gene, the MYC family genes may be transduced. Furthermore, in addition to such 4 genes, at least one gene which is relatively strongly expressed in the cell having the ability to form the stratified epithelial tissue may also be transduced. As differences in the proliferative potency and the terminal differentiative potency had been confirmed between the induced fibroblast of Example 1 and the induced fibroblast of Example 2, the property and ability of the cell to be prepared, e.g. proliferative potency, terminal differentiative potency, etc. could be regulated depending on the combination of genes to be concomitantly transduced, and usefulness of adjustment for the transgene depending on the intended purpose was confirmed.

LIST OF CITATIONS

Citation 1: Shalom-Feuerstein R, Lena A M, Zhou H, De La Forest Divonne S, Van Bokhoven H, Candi E, Melino G, Aberdam D. Cell Death Differ. 2011; 18(5):887-96.

Citation 2: Kurita M, Okazaki M, Kaminishi-Tanikawa A, Niikura M, Takushima A, Harii K. Connect Tissue Res. 2012; 53(5):349-54.

Citation 3: Kurita M, Okazaki M, Fujino T, Takushima A, Harii K. Biochem Biophys Res Commun. 2011 May 27; 409(1):103-7.

Citation 4: Chapman S1, Liu X, Meyers C, Schlegel R, McBride A A. J Clin Invest. 2010 July; 120(7):2619-26

Citation 5: Okazaki M, Yoshimura K, Fujiwara H, Suzuki Y, Harii K. Plast Reconstr Surg. 2003 September; 112(3):784-92.

Citation 6: Okazaki M, Yoshimura K, Suzuki Y, Harii K. Plast Reconstr Surg. 2003 September; 112(3):784-92.

What is claimed is:

1. A production method of a cell capable of forming a stratified epithelial tissue, comprising introducing GATA3 gene, TFAP2A gene, GRHL2 gene, TP63 gene, BNC1 gene, EHF gene, ZNF165 gene, c-MYC gene, OVOL1 gene, OVOL2 gene, ESRP1 gene, ID1 gene, GRHL1 gene, GRHL3 gene, DNP63A gene, MAPK13 gene, ARNTL2 gene, LASS3 gene, ZNF750 gene, ZBED2 gene, SOX7 gene, SOX9 gene, FOXQ1 gene, PPP1R13L gene, and KLF4 gene, into a somatic cell and thereby directly converting the somatic cell into the cell capable of forming the stratified epithelial tissue.

2. The production method of claim 1, further comprising introducing IRX2 gene and IRX4 gene into the somatic cell.

3. The production method of claim 1, wherein the somatic cell is derived from a human.

4. The production method of claim 1, wherein the somatic cell is a skin fibroblast.

5. The production method of claim 1, wherein the somatic cell is an adipose-tissue derived stromal cell.

6. The production method of claim 1, wherein the somatic cell is a mononuclear cell in a peripheral circulating blood.

* * * * *